(12) United States Patent
Yan et al.

(10) Patent No.: US 8,449,891 B2
(45) Date of Patent: May 28, 2013

(54) RECOMBINANT FLAGELLIN PROTEIN AND PREPARATION AND USE THEREOF

(75) Inventors: Huimin Yan, Wuhan (CN); Fang Liu, Wuhan (CN); Jingyi Yang, Wuhan (CN)

(73) Assignee: Wuhan Institute of Virology, Chinese Academy of Sciences, Wuhan (CN)

( * ) Notice: Subject to any disclaimer, the term of this patent is extended or adjusted under 35 U.S.C. 154(b) by 50 days.

(21) Appl. No.: 13/122,409

(22) PCT Filed: Aug. 9, 2010

(86) PCT No.: PCT/CN2010/075805
§ 371 (c)(1),
(2), (4) Date: Apr. 2, 2011

(87) PCT Pub. No.: WO2011/063660
PCT Pub. Date: Jun. 3, 2011

(65) Prior Publication Data
US 2011/0230643 A1    Sep. 22, 2011

(30) Foreign Application Priority Data

Nov. 27, 2009 (CN) .......................... 2009 1 0194284

(51) Int. Cl.
| C07K 1/00 | (2006.01) |
| C07K 14/00 | (2006.01) |
| C07K 17/00 | (2006.01) |
| A61K 39/00 | (2006.01) |
| A61K 39/02 | (2006.01) |
| A61K 39/112 | (2006.01) |
| A61K 39/38 | (2006.01) |

(52) U.S. Cl.
USPC ................. 424/190.1; 424/184.1; 424/185.1; 424/234.1; 424/258.1; 530/350

(58) Field of Classification Search
None
See application file for complete search history.

(56) References Cited

FOREIGN PATENT DOCUMENTS
WO    WO 2009128950    * 10/2009

OTHER PUBLICATIONS

Liu et al. Biochemical and Biophysical Research Communications 392:582-587 available online Jan. 25, 2010.*
Nempont et al. J. Immunol. 2008; 181:2036-2043.*
Uniprot Accession # Q56086. *Salmonella typhi* FliC. Nov. 1, 1996.*

* cited by examiner

*Primary Examiner* — Oluwatosin Ogunbiyi
(74) *Attorney, Agent, or Firm* — George D. Liu; Ronda IP Agent Co., Ltd

(57) ABSTRACT

The present invention provides an optimized recombinant flagellin protein and preparation and use thereof. The protein is with a deletion in the hypervariable region, said hypervariable region is the region from 180 to 400 amino acid of the flagellin protein, and the proteins include FliCΔ190-278, FliCΔ220-320 or FliCΔ180-400. The method of preparing said protein, comprising introducing a deletion into the hypervariable region of the flagellin protein. First constructed the flagellin protein recombinant plasmid, and then used it as template to construct the flagellin deletion cloning, and expressed and purified. The present invention also provides the use of the recombinant flagellin protein as adjuvant. The recombinant flagellin protein in present invention decreases the potential risks it may have, and decreases its antigenicity and immunogenicity and the inflammatory response induced by it, through deleting its main areas of immunogenicity and antigen activity.

2 Claims, 18 Drawing Sheets

US 8,449,891 B2

RECOMBINANT FLAGELLIN PROTEIN AND PREPARATION AND USE THEREOF

FIELD OF THE INVENTION

The present invention relates to the field of biotechnology, and more particularly, relates to an optimized recombinant flagellin protein and preparation and use thereof.

BACKGROUND OF THE INVENTION

It is known that flagellin proteins originated from pathogenic bacteria have immune adjuvant effects. The flagellin protein binds to Toll-like receptors (TLRs) 5, activating the NF-κB pathway and then triggering innate immunity and further inducing specific immunity. The mixture or fusion of flagellin protein with a target antigen can significantly enhance the immune responses to the target antigen upon immunization, and can achieve the effects of resisting pathogenic microorganisms carrying the target antigen. But because the flagellin protein originates from pathogenic bacteria, it may have potential risk, and it also can cause inflammatory response, induce a large amount of immune response against itself, lead to possible tolerance and other possible immunological side effects.

SUMMARY OF THE INVENTION

The present invention provides an optimized recombinant flagellin protein, and uses it as adjuvant; while ensuring the maintenance of its adjuvant activity, the optimized recombinant flagellin protein has decreased antigenicity, immunogenicity and inflammatory response.

The first aspect of the present invention provides a recombinant flagellin protein with a deletion in the hypervariable region, where the hypervariable region consists of amino acids from 180 to 400.

Preferably, the recombinant flagellin protein includes FliCΔ190-278, FliCΔ220-320 or FliCΔ180-400.

The second aspect of the present invention provides a method of preparing recombinant flagellin protein, including making deletions in the hypervariable region of the flagellin protein, where the hypervariable region consists of amino acids from 180 to 400.

Specifically, the preparation method comprises the following steps:

(1) construction of the flagellin protein recombinant plasmid;

(2) construction of the flagellin deletion clones by using the flagellin protein recombinant plasmid obtained from step 1 as template, and expression and purification.

Preferred, the template of above step (1) construction of the flagellin protein recombinant plasmid is the genome of human *Salmonella enterica* J341, the primers are the sequences shown in SEQ ID NO: 1 and SEQ ID NO: 2, the ligation vector is the pET28.

Preferred, the primers of above step (2) construction of the flagellin deletion clones are the sequences shown in SEQ ID NO: 3 to SEQ ID NO: 6, to obtain the recombinant flagellin protein FliCΔ190-278; or the sequences shown in SEQ ID NO: 7 to SEQ ID NO: 10, to obtain the recombinant flagellin protein FliCΔ220-320; or the sequences shown in SEQ ID NO: 11 to SEQ ID NO: 14, to obtain the recombinant flagellin protein FliCΔ180-400. Details are shown in the embodiments.

The present invention also provides a use of the recombinant flagellin protein as adjuvant. Because the adjuvant was obtained by manipulating the flagellin protein, the antigenicity and immunogenicity and inflammatory response of the recombinant flagellin protein were decreased, while its adjuvant activity is maintained.

Compared to the prior art, the present invention has the following beneficial effects:

By manipulating the flagellin protein with deletion of its main immunogenicity and antigenicity regions, its antigenicity and immunogenicity and inflammatory response are decreased.

DETAILED DESCRIPTION OF THE INVENTION

Figure 1:
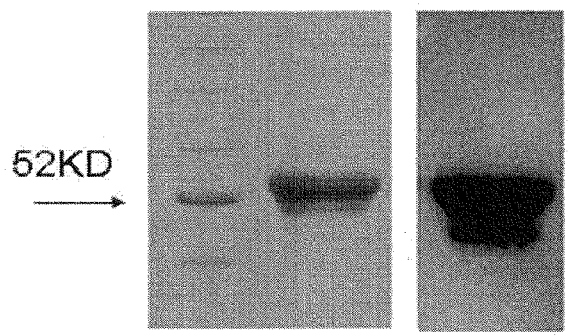
FIG. 1 shows the pictures of purification and verification of the expressed flagellin protein by SDS-PAGE and western blot respectively.

The present invention will be further illustrated combining with embodiments as follows. It should be noted that the scope of the present invention is not limited by the embodiments.

The experimental method without given specific conditions is referred to the conventional conditions, such as the conditions described in Sambrook and other molecular cloning experiments manuals.

Embodiment 1

Construction of Cloning (1) Construction of FliC Recombinant Plasmid

FliC (SEQ ID NO. 17) was obtained by PCR amplification from the genome of human *Salmonella enterica* J341, using the primer1/primer2 (SEQ ID NOs. 1/2) as primers (primer sequences see Table 1). The NcoI and XhoI restriction sites in the primers are underlined. In order to facilitate purification of recombinant protein, the stop codon TAA of flic gene was deleted when the primer2 was designed, thus making a 6-histidine tag which after the restriction site XhoI of vector pET28 for fusion expression. PCR products were double digested with NcoI and XhoI, and were ligated with vector pET28a which also was double digested and linearized. Ligated products were transformed into BL21 (DE3) star; positive clones were picked for restriction enzyme digestion and sequencing, the correct recombinant plasmid was named FliC, and its expression products had the 6-histidine tag at C-terminal.

(2) Construction of the Flagellin Deletion Clones of FliCΔ180-400 (SEQ ID NO. 18), FliCΔ190-278 (SEQ ID NO. 19) and FliCΔ220-320 (SEQ ID NO. 20)

Construction of the FliCΔ180-400: fragment FliC (1-180AA) and FliC (400-560AA) were amplified, by using the FliC1 recombinant plasmid as template, and respectively using the primer21/primer22 (SEQ ID NO. 3/4), primer23/ primer24 (SEQ ID NO. 5/6) as the primers (primer sequences see Table 1, Table 1 shows the oligonucleotide primers). The 5' end of primer21 and primer22 were respectively designed with restriction sites NcoI and EcoRI, the 5' end of primer23 and primer24 were respectively designed with restriction sites EcoRI and XhoI. After the PCR products were digested with NcoI/EcoRI and EcoRI/XhoI, both the C-terminal of FliC (1-180AA) fragment and the N-terminal of FliC (400-560AA) fragment produced the same EcoRI sticky ends. The restriction digested fragments were placed at 4° C. to ligate for 1 hour according to the ratio of 1:1, and the ligated products were purified by running on gel. The purified products ligated with the vector pET28a which had been double digested and linearized by NcoI and XhoI. Ligated products were transformed into BL21 (DE3) star; positive clones were picked for restriction enzyme digestion and sequencing, the correct recombinant plasmid was named FliCΔ180-400.

Construction of the FliCΔ190-278 and FliCΔ220-320, PCR amplification was carried out, by using primer13/ primer14 (SEQ ID NOs. 7/8) and primer15/primer16 (SEQ ID NOs. 9/10) as well as primer17/primer18 (SEQ ID NOs. 11/12) and primer19/primer20 (SEQ ID NOs. 13/14) as primers (primer sequences see Table 1) respectively. The construction process was the same as that of the recombinant plasmid FliCΔ180-400. FliC297-471 (SEQ ID NO. 21) was constructed using primers 31/32 (SEQ ID NOs. 15/15) following the same protocol as described above.

TABLE 1

| plasmids | primers | sequences (5'-3') |
|---|---|---|
| FliC1 | primer1 | CGCGCCATGGCACAAGTCATTAATACAAACA (SEQ ID NO. 1) |
| | Primer2 | CGGTCTCGAGACGCAGTAAAGAGAGGACGTTTTG (SEQ ID NO. 2) |
| FliCΔ190-278 | Primer13 | CCTACGCCATGGCACAAGTCATTAATACA (SEQ ID NO. 3) |
| | Primer14 | GGCAGTGAATTCTTTATCAACGGTTACAGCAGT (SEQ ID NO. 4) |
| | Primer15 | CGATGCGAATTCATAACCCACAACCAAATTGCT (SEQ ID NO. 5) |
| | Primer16 | GATCCGCTCGAGACGCAGTAAAGAGAGGACGTT (SEQ ID NO. 6) |
| FliCΔ220-320 | Primer17 | CGCGTTCCATGGCACAAGTCATTAATACA (SEQ ID NO. 7) |
| | Primer18 | CCAGTAGAATTCAGTAACCCCCGTTGCACCACC (SEQ ID NO. 8) |
| | Primer19 | CCAGTGGAATTCTTTGAGGATAAAAACGGTAAG (SEQ ID NO. 9) |
| | Primer20 | GCCGATCTCGAGACGCAGTAAAGAGAGGACGTTTTG (SEQ ID NO. 10) |
| FliCΔ180-400 | Primer21 | CGCGTTCCATGGCACAAGTCATTAATACA (SEQ ID NO. 11) |
| | Primer22 | GGCTTGGAATTCGGTGTAGGCATCTTGGACATT (SEQ ID NO. 12) |
| | Primer23 | GGCACGGAATTCAACTTCAGAACAGGCGGTGAG (SEQ ID NO. 13) |
| | Primer24 | GCCGATCTCGAGACGCAGTAAAGAGAGGACGTTTTG (SEQ ID NO. 14) |

TABLE 1-continued

| plasmids | primers | sequences (5'-3') |
|---|---|---|
| FliC297-471 | Primer31 | CTCGATCCATGGTTGCGGCTCAACTTG CTGCA (SEQ ID NO. 15) |
| | Primer32 | GGCTGACTCGAGTGCGTAGTCGGAATC TTCGAT (SEQ ID NO. 16) |

Embodiment 2

Expression and Purification of Recombinant Proteins

A single colony was picked and the bacteria cells were incubated overnight (37° C., 220 rpm), with kanamycin 50 μg/ml. It was transferred at 1% into fresh 2YT medium (tryptone 16 g/L, yeast extract 10 g/L, NaCl 5 g/L) (37° C., 220 rpm) in the next day, with kanamycin 50 μg/ml. After transferred for 2-3 h (the bacteria grew into early—middle logarithmic growth phase), IPTG was added to induce expression (final concentration was 0.5 mM). After 4-5 h of induced expression, the bacteria cells were centrifuged and collected, resuspended in 20 ml 1× binding buffer (20 mM Tris-HCl, 500 mM NaCl, 5 mM imidazole, pH7.9) per gram of bacteria, the bacteria cells were sonicated, centrifuged (13000 rpm, 20 min, 4° C.). The supernatant was purified with nickel column. The combined recombinant protein was eluted with elution buffer (20 mM Tris-HCl, 500 mM NaCl, 250 mM imidazole, pH7.9). The purity and molecular size of the collected recombinant protein was determined by sodium dodecyl sulfate-polyacrylamide polyacrylamide gel electrophoresis (SDS-PAGE).

In western blot analysis, the purified flagellin protein was transferred onto nitrocellulose membrane through SDS-PAGE, blocked in 1% skim milk powder at room temperature for 2 h, and then the membrane was incubated with mouse anti-his-tag monoclonal antibody (1:2000 dilution), incubated at 4° C. overnight; the membrane was washed with TBST for five times, 10 min per time, and was incubated with HRP-conjugated goat anti-mouse anti-IgG antibody (1:100, 000 dilution), at room temperature for 1 h, and then washed with TBST for five times. Detected with chemiluminescence solution (Pierce) for 5 min and observed the result.

The result is shown in FIG. 1. FIG. 1 shows the result figures of purified protein verification by SDS-PAGE and western blot respectively. 0.5 mmol/L IPTG was added when the bacteria was incubated to OD600 value of 0.6-1.0 at 37° C. After 4 h of induced expression at 37° C., the bacteria cell was collected, sonicated, and purified with nickel column. The purified protein was verificated by SDS-PAGE and western blot. Shown in FIG. 1, an approximate 52 KD protein was successfully obtained.

Removal endotoxin from the recombinant protein and detection, as follows: affinity chromatography: the purified flagellin protein was removed of endotoxin with polymyxin B affinity column (Pierce), and detected residual endotoxin content with lachypleus amebocyte lysate, the residual endotoxin content <0.06 EU/mg.

Embodiment 3

MCP-1 and IL-8 Release Assay

According to the literature, Caco-2 cells constitutively expressed TLR5, flagellin was the ligand of TLR5, the Caco-2 cells stimulated by flagellin could be induced to release high level of chemokines IL-8 and MCP-1. To research whether the flagellin originated from Salmonella J341 also had stimulating activity, the Caco-2 cells were seeded in 24 well plates, $2 \times 10^5$/well, for 7-21 days to make the cells become polarized. Before stimulation, the cells were kept starving for 8-12 h, and then the starvation medium was removed when stimulating. The cells were washed twice with fresh serum-free medium. Samples were diluted with serum-free medium at concentration of FliC 0.1, 1, 10, 100, 1000 ng/ml respectively. The diluted samples were loaded into each well, 1 ml/well, each treated 4 wells. Negative control cells were stimulated with FliC297-471 and serum-free medium respectively, the culture medium were collected after 6 hours, and centrifuged for 10 min at 2000 rpm. The supernatant was obtained to detect cytokines IL-8 and MCP-1.

Figure 2:
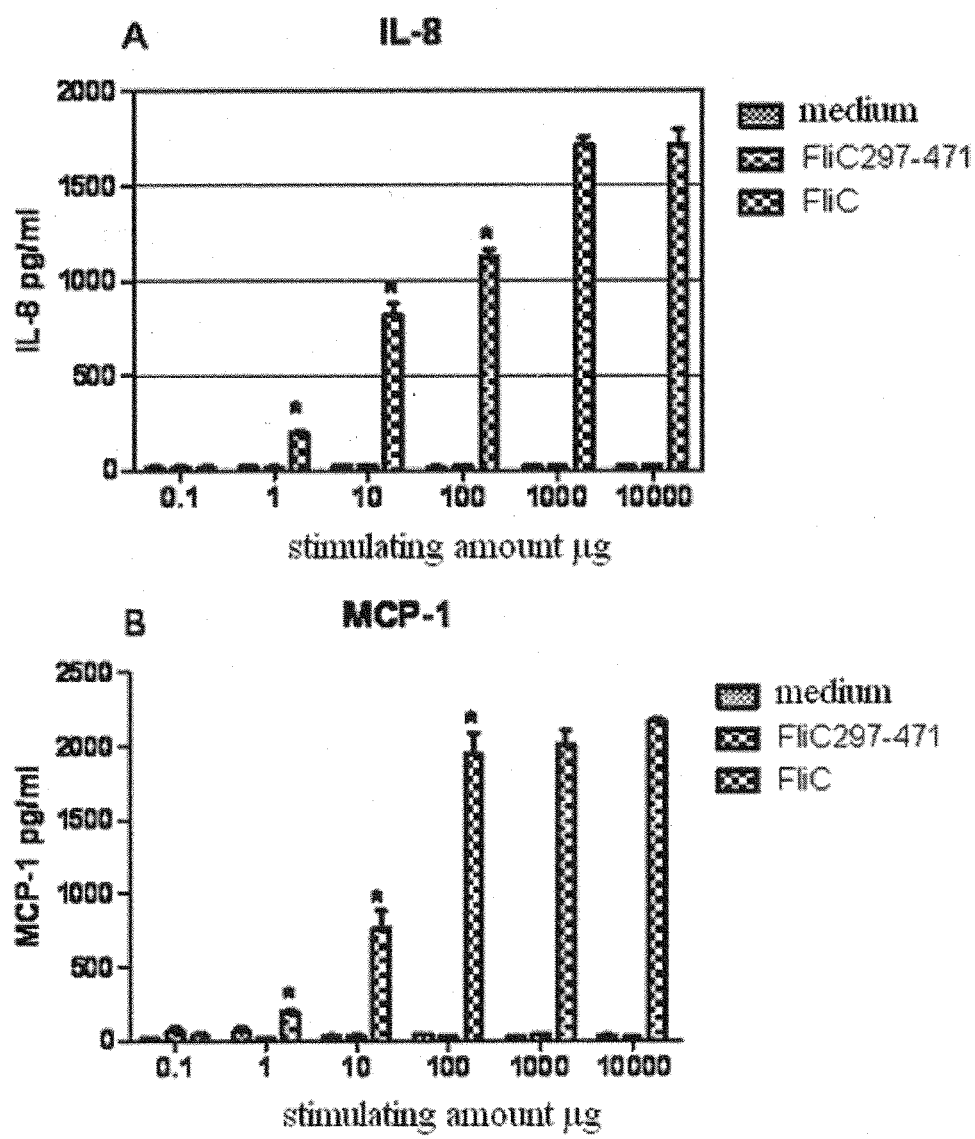
FIG. 2 shows the IL-8 and MCP-1 release level of Caco-2 cells induced by FliC or FliC297-471 stimulation respectively, wherein (A) shows the IL-8 release level of Caco-2 cells induced by FliC or FliC297-471 stimulation respectively, and (B) shows the MCP-1 release level of Caco-2 cells induced by FliC or FliC297-471 stimulation respectively.

The result is shown in FIG. 2. FIG. 2 shows the IL-8 and MCP-1 release level of Caco-2 cells induced by FliC stimulation, wherein (A) shows the IL-8 release level of Caco-2 cells induced by FliC stimulation, and (B) shows the MCP-1 release level of Caco-2 cells induced by FliC stimulation. Shown in FIG. 2, compared with the control, FliC stimulation induced Caco-2 cells to release high level of IL-8 and MCP-1, while they were consistent, low dose (<100 ng/ml) stimulation induced obvious dose effect, and when the dose >1000 ng/ml the stimulating activity reached saturation. Considering the residual endotoxin may interfere with the stimulating activity of flagellin, the control cells were stimulated with FliC297-471 without stimulating activity which had been expressed and purified as same, to confirm the stimulating activity was specific of flagellin. The result showed that there was no difference between the FliC297-471 treated cells and serum-free medium only added cells, thus indicated that the stimulating activity was specific of flagellin.

Embodiment 4

Experiment in Mice for Investigating the Adjuvant Activity of Flagellin Protein 6-8 weeks old BALB/c or C57BL/6 mice were purchased from Center For Disease Control of Hubei province, and raised at the animal experiment center of Wuhan Institute of Virology, Chinese Academy of Sciences (CAS). Before immunization, they were fed 3-7 days to adapt to the environment. Intranasal immunization: the mice were anesthetized with 120-150 μl (10 mg/ml) pentobarbital via intraperitoneal injection, the sample was diluted with endotoxin-free PBS. Total volume of intranasal was 10 μl, 5 μl/once, for twice, ensuring the sample to be fully absorbed. Immunization strategy: primary immunization (0 week)—first booster immunization (4th week)—second booster immunization (6th week), decide whether to booster and the booster times according to situation. The mice were killed 2 weeks after the last immunization, their blood and saliva samples, vaginal samples were collected. The mice should be kept fasting (not fasting in liquid) 1 day. Saliva samples: first injected carbachol (200 μg/ml), 100 μl/mouse, observed salivary secretion in mice, 1~2 min later, the secretion of saliva was absorbed into 1.5 ml EP; vaginal samples: vaginal of mice were lavaged with 90~100 μl PBS, 30 μl/once, for 3 times; bronchoalveolar lavage fluid (BALF): bronchoalveolar of mice were lavaged with 1 ml PBS, 500 μl/once, for 2 times. Blood samples were incubated at 4° C. for 3~4 h, and centrifuged for 30 min at 1500 rpm, the supernatant was saved at −80° C. for subsequence detection. Mucosal samples were centrifuged for 10 min at 10000 rpm, the supernatant was saved at −80° C. for subsequence detection.

Figure 3:
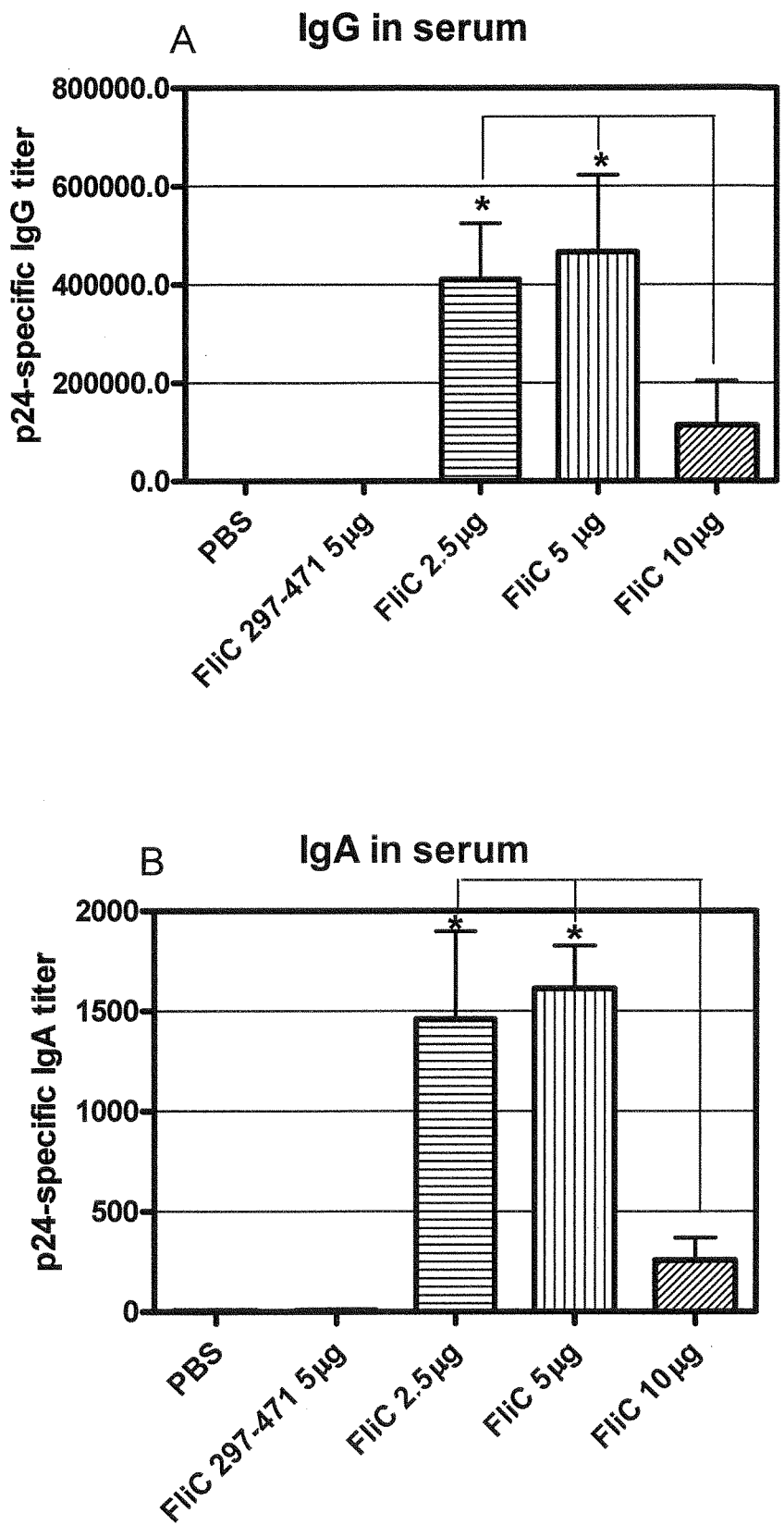
FIG. 3 shows the results of FliC adjuvant activity at different concentrations, wherein (A) shows the p24-specific IgG titers in sera, (B) the p24-specific IgA titers in sera, (C) the p24-specific IgA titers in salivary, (D) the p24-specific IgA titers in vaginal samples, and (E) the p24-specific and FliC-specific IgG titers in sera.
Figure 3:
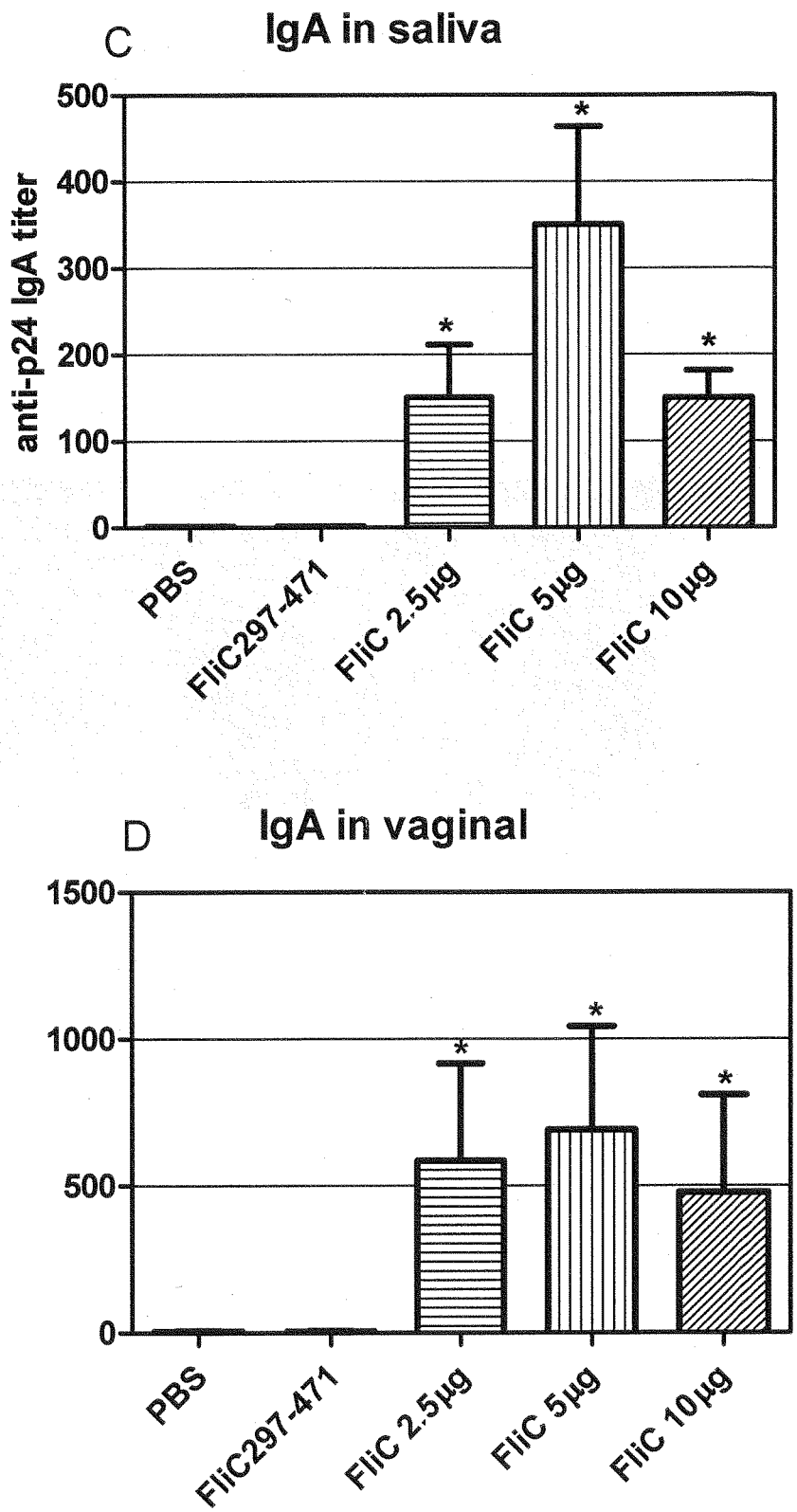

To further investigate the adjuvant activity of flagellin protein, HIV core protein p24 10 ug was used as model antigen. 6-8 weeks old BALB/c mice were divided into 5 groups, intranasal immunized with PBS, FliC297-471, FliC 2.5, 5, 10 ug respectively, booster immunized one time after 4 weeks, killed 2 weeks after the last immunization. The serum and mucosal samples were obtained to detect titer of p24-specific and FliC-specific antibody by ELISA. The results are shown in FIG. 3, FIG. 3 shows the related experimental results of FliC adjuvant activity, wherein (A) shows the comparison results of p24-specific IgG titers in sera, (B) shows the comparison results of p24-specific IgA titers in sera, (C) shows the comparison results of p24-specific IgA titers in salivary, (D) shows the comparison results of IgA titers in vaginal, and (E) shows the comparison results of IgG titers in sera. The results of FIG. 3 show that, compared with PBS and FliC297-471 control groups, FliC immunized group significantly enhanced the titers of p24-specific IgG, IgA in sera and IgA in mucosal samples (FIG. 3, A, B, C and D), indicating that FliC had strong adjuvant activity. Surprisingly, we found that when FliC was 10 μg, the titer of p24-specific serum IgG and IgA was lower than that of low dose of 2.5 μg and 5 μg. To clarify this reason, we further analyzed the titers of FliC-specific IgG in sera. It was found that, the titers of FliC-specific IgG was 2-3 times higher than that of p24-specific IgG, particularly when FliC was 10 μg, the titer of FliC-specific IgG was 10 times higher than that of p24-specific IgG, (FIG. 3, E), indicating strong immunogenicity of FliC might interfere with the immune response of target antigens.

Embodiment 5

Solubility Studies of Flagellin Protein and Deletion Clones

Figure 4:
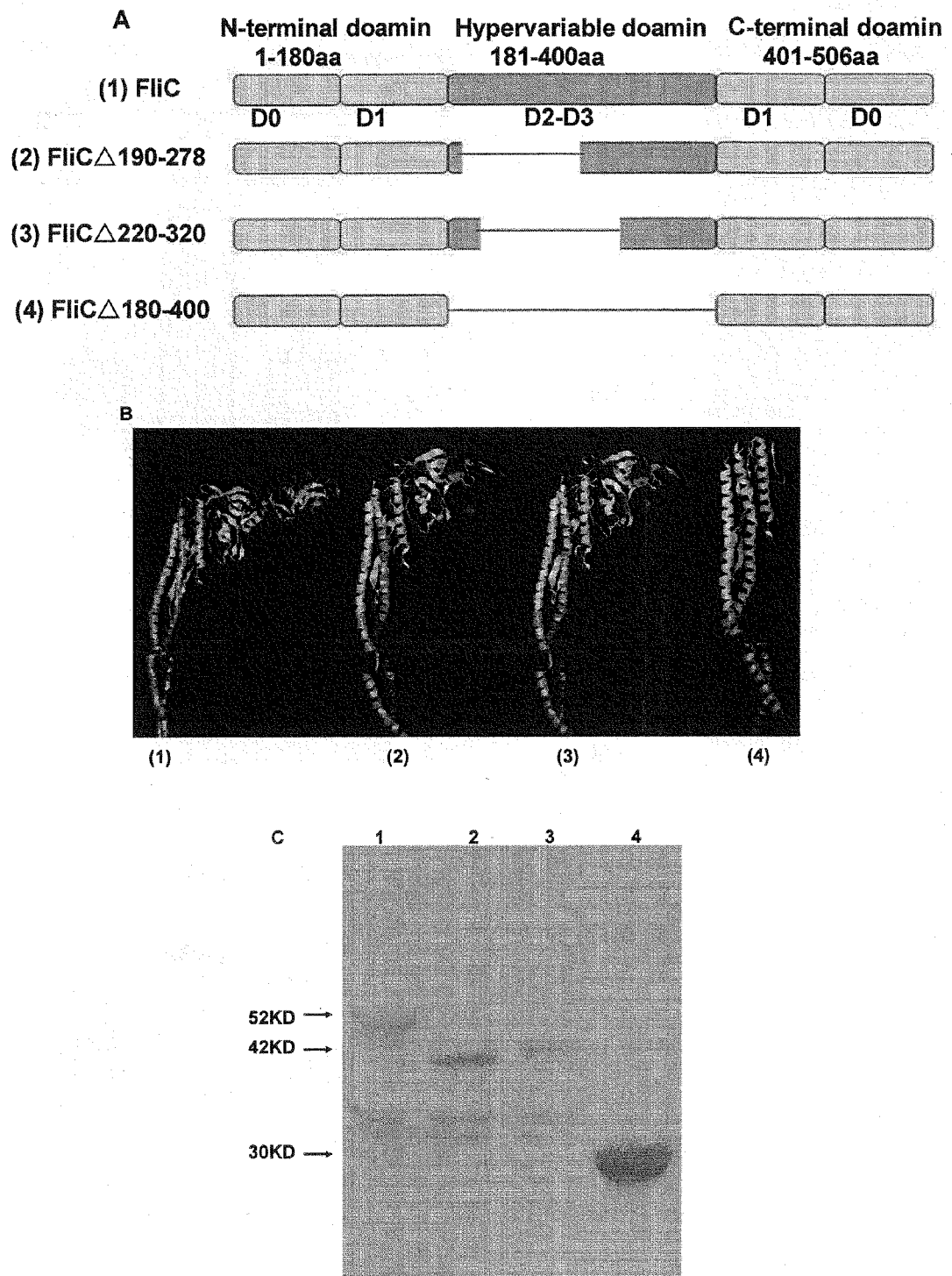
FIG. 4 shows the expression and purification of recombinant flagellin proteins, wherein (A) shows the structure diagrams of three deletion proteins, (B) the modeled three dimensional structures of FliC and three deletion proteins, (C) the SDS-PAGE electrophoretogram of FliC and three deletion proteins in the insoluble fraction, (D) the SDS PAGE electrophoretogram of FliC and three deletion proteins in the soluble fraction, and (E) the Western blot of FliC and three deletion proteins; where (1), (2), (3) and (4) in (B) to (E) are corresponding to the ones shown in (A)
Figure 4:
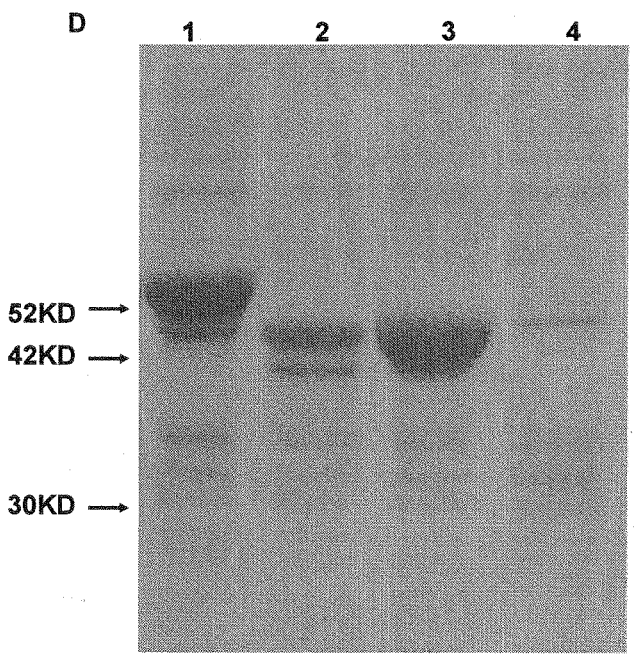
Figure 4:
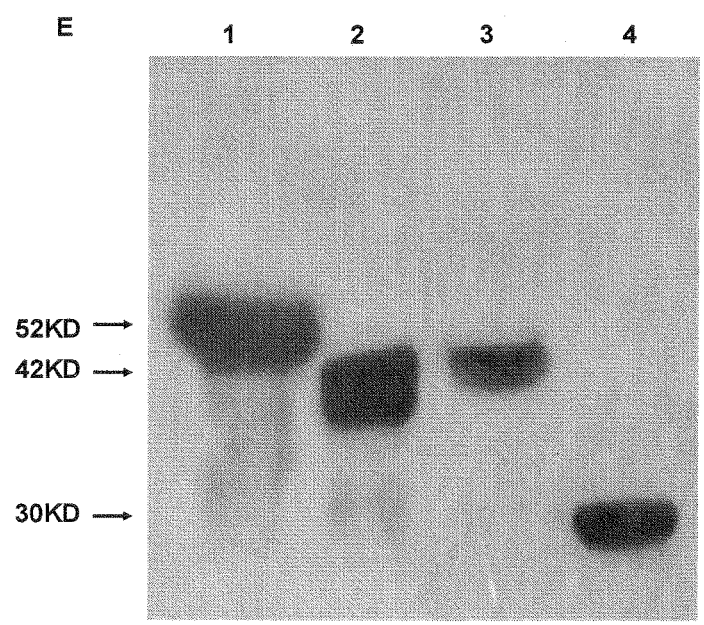

In view of strong immunogenicity of FliC, and in view of its structure, namely N terminal (about 170 amino acids) and C terminal (about 100 amino acids) were very conservative and the TLR5 binding region, closely related with adjuvant activity, while the central regions (18-0400 amino acids) were varied greatly both in amino acid sequence and size aspects, it was generally believed that they were related to the antigenicity, protein folding and adhesion of the flagellin protein. According to the literature, deletion of central hypervariable region does not affect the adjuvant activity of flagellin. We hypothesized that flagellin still had good adjuvant activity without the central 18-400 amino acid sequence. Based on this, we first constructed the flagellin deletion cloning FliCΔ180-400, but the FliCΔ180-400 structure was found unstable, it was expressed in inclusion body formation (FIG. 4, C, D and E), FIG. 4 shows the figures of related experiment of stability of hypervariable region deleted flagellin protein, wherein (A) shows the structure diagram of three constructed proteins with deletion, (B) shows the three dimensional structure of three constructed proteins being deleted, (C) shows the electrophoretogram of FliC and deletion clones in the insoluble fraction, (D) shows the electrophoretogram of FliC and deletion clones in the soluble fraction, and (E) shows the Western blot of FliC and deletion clones. Although protein dissolution could be obtained from inclusion body by denaturation and renaturation, but it was time-consuming and laborious, while the protein was also easy to get denaturated in the process of protein operation, and it is not advisable, particularly to the application-based protein such as adjuvant. Through consulting to related literature and using bioinformatics methods, we found that the greatest change in flagellin amino acid sequence placed in the region 190-350, wherein the hypervariable regions were concentrated at 190-280 and 220-320 two regions. So we also constructed FliCΔ190-278 and FliCΔ220-320 two clones, which respectively deleted 190-278 and 220-320 amino acids. Fortunately, these two clones with partially deleted hypervariable region were of good solubility (FIG. 4, C, D and E).

Embodiment 6

Figure 5:
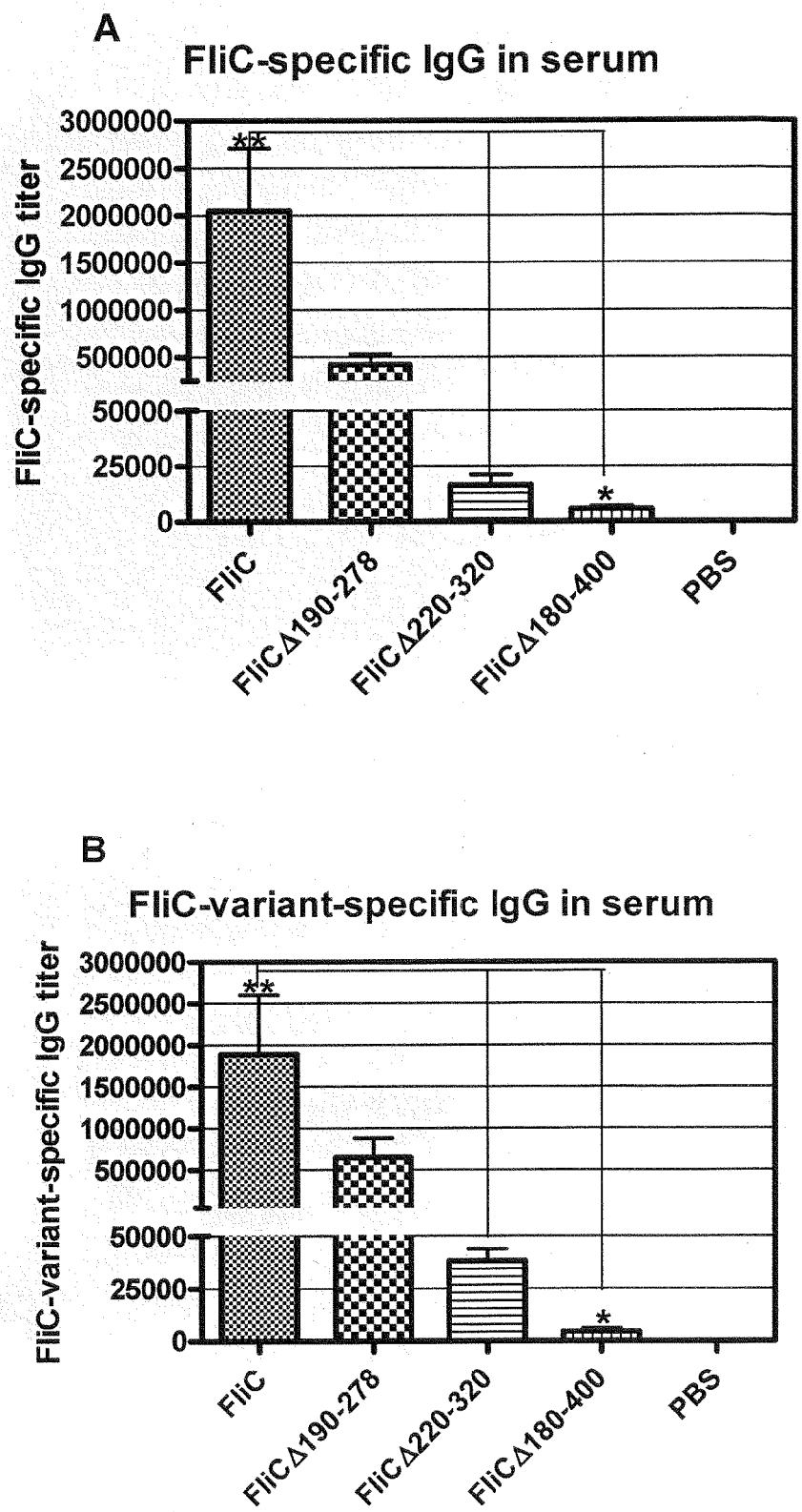
FIG. 5 shows the experimental results of FliC-specific and FliC-recombinant protein-specific IgG titers in the sera, wherein (A) shows the FliC-specific IgG titers in the sera of mice immunized with FliC or different FliC-recombinant proteins respectively by ELISA, and (B) the FliC-specific or FliC-recombinant protein-specific IgG titers in the sera by ELISA.

Experiment of Partial Deletion of Hypervariable Region Amino Acid Sequence Significantly Decreased the Antigenicity and Immunogenicity of Flagellin To analyze the antigenicity and immunogenicity of deletion recombinant clones, BALB/c mice were intranasal immunized with FliC, FliCΔ190-278, FliCΔ220-320 and FliCΔ180-400 respectively, 2.5 ug/mouse, 5 mice/group, booster immunized one time after been primary immunized for 4 weeks, killed 2 weeks later. The blood samples were drawn from orbit. The titer of FliC-specific IgG and FliC-recombinant cloning-specific IgG in the serum was detected by ELISA. The result is shown in FIG. 5, FIG. 5 shows the experimental result figures of the titer detection of FliC-specific IgG and FliC-recombinant cloning-specific IgG in the serum, wherein, (A) shows the comparison of titer detection of FliC-specific IgG in the serum by ELISA, and (B) shows the comparison of titer detection of FliC-recombinant cloning-specific IgG in the serum by ELISA. Compared with full-length flagellin FliC, deletion recombinant cloning all decreased flagellin's antigenicity and immunogenicity (FIG. 5, A and B), but FliCΔ190-278 was decreased 2-3 times compared to full-length, while FliCΔ220-320 and FliCΔ180-400 were decreased 100-200 times compared to full-length, eaching a significant difference (p<0.05) (FIG. 5, A and B).

Embodiment 7

Figure 6:
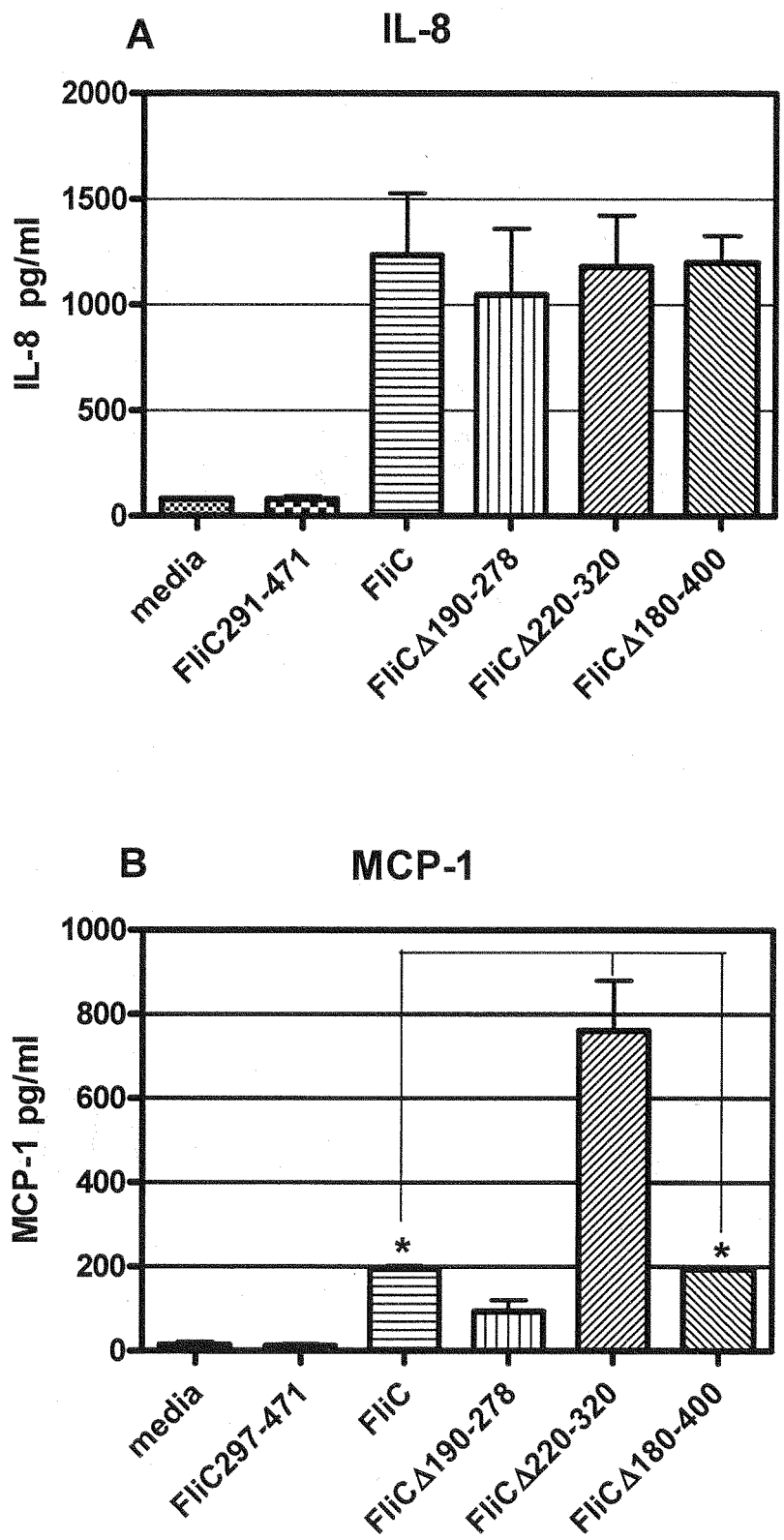
FIG. 6 shows the ELISA results of IL-8 and MCP-1 quantity in the supernatants of Caco-2 cells stimulated respectively with FliC, FliCΔ190-278, FliCΔ220-320 or FliCΔ180-400 at different concentrations (0.1, 1, 10, 100, 1000, 10000 ng/ml), wherein (A) shows the IL-8 levels, and (B) the MCP-1 level.

FliCΔ190-278, FliCΔ220-320 and FliCΔ180-400 had Good Cell Stimulating Activity In Vitro Whether the partial deletion or complete deletion of hypervariable region affected the structure of flagellin or the binding to TLR5, we detected the stimulation ability to Caco-2 cell of every deletion clones, using Caco-2 cell as model cell, and using IL-8 and MCP-1 as detect indexes. The deletion recombinant clones FliCΔ190-278, FliCΔ220-320 and FliCΔ180-400 were used to stimulate Caco-2 cell at different concentrations (0.1, 1, 10, 100, 1000, 10000 ng/ml), and the IL-8 and MCP-1 were detected by ELISA. The results are shown in FIG. 6. FIG. 6 shows the detection results of IL-8 and MCP-1 by ELISA after the deletion recombinant clones FliCΔ190-278, FliCΔ220-320 and FliCΔ180-400 were used to stimulate Caco-2 cell at different concentrations (0.1, 1, 10, 100, 1000, 10000 ng/ml), wherein (A) shows the detection results of IL-8 by ELISA, and (B) shows the detection results of MCP-1 by ELISA. It was found that, the deletion recombinant clones all had good cell stimulating activity at different concentration conditions. While, it was found that, when using low doses of 10 ng/ml, FliCΔ220-320 had good stimulating activity, by which the IL-8 level was induction released was equivalent with that of full length flagellin protein FliC, significantly higher than that of FliCΔ190-278 and FliCΔ180-400 (FIG. 6, A). Meanwhile, it was unexpectedly found in MCP-1 detection that, the MCP-1 induction released by deletion cloning FliCΔ190-278, FliCΔ220-320 and FliCΔ180-400 was significantly higher than that of full length flagellin protein FliC (FIG. 6, B) (p<0.05). It was speculated that, there may exist some kind of negative regulator in hypervariable region, but no relevant literature had been reported yet.

Embodiment 8

FliCΔ220-320 Had Better Mucosal Adjuvant Activity Than FliCΔ190-278 and FliCΔ180-400

Figure 7:
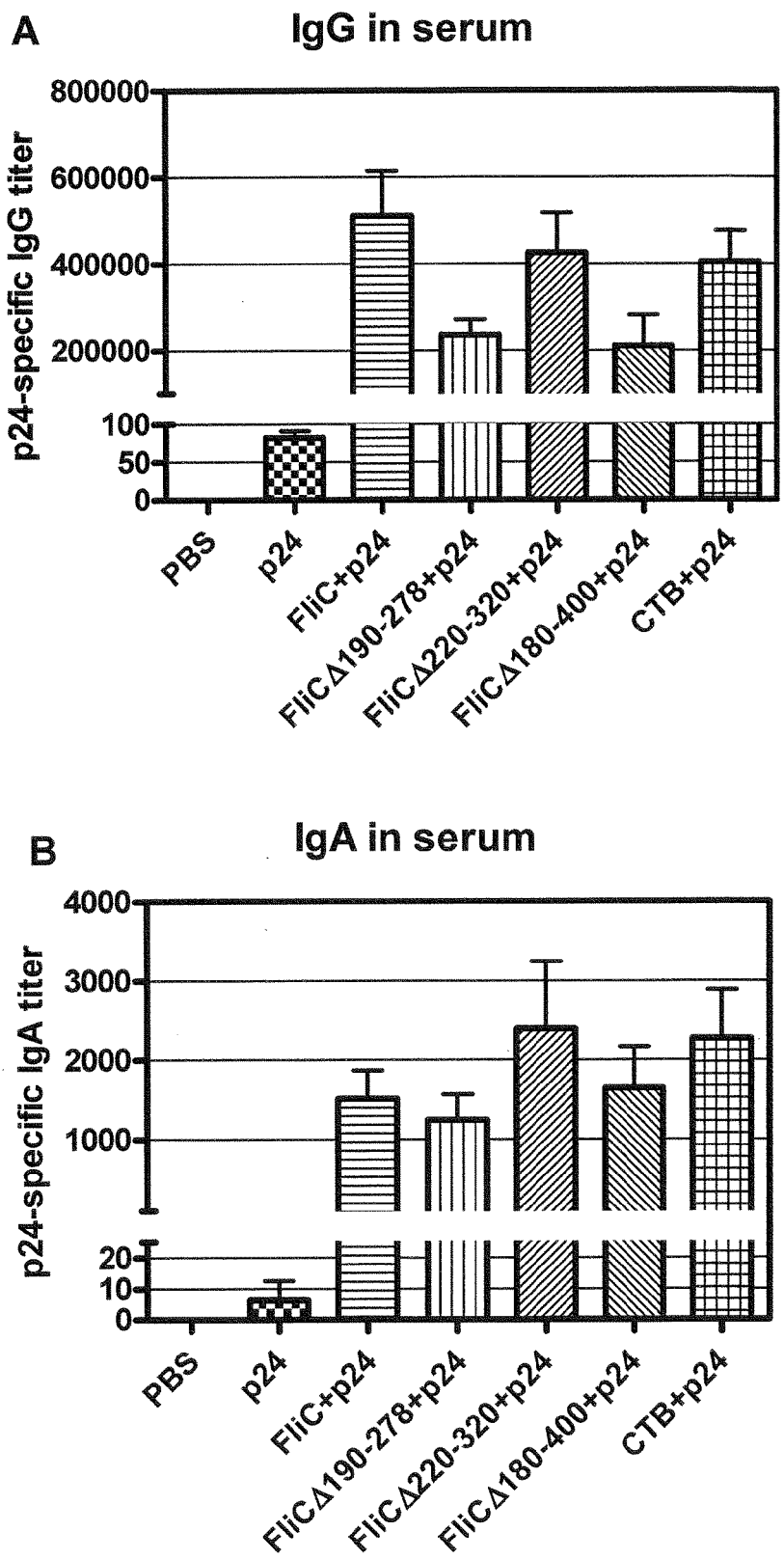
FIG. 7 shows the p24-specific antibody titers in sera, saliva, or vaginal samples from BalB/c mice immunized with p24 as antigen (10 μg/mouse) in mixture with FliC, FliCΔ190-278, FliCΔ220-320 or FliCΔ180-400 (2.5 μg/mouse) respectively, wherein (A) shows the p24-specific IgG titers in sera, (B) the p24-specific IgA titers in sera, (C) the p24-specific IgA titers in saliva, and (D) the p24-specific IgA titers in vaginal samples.
Figure 7:
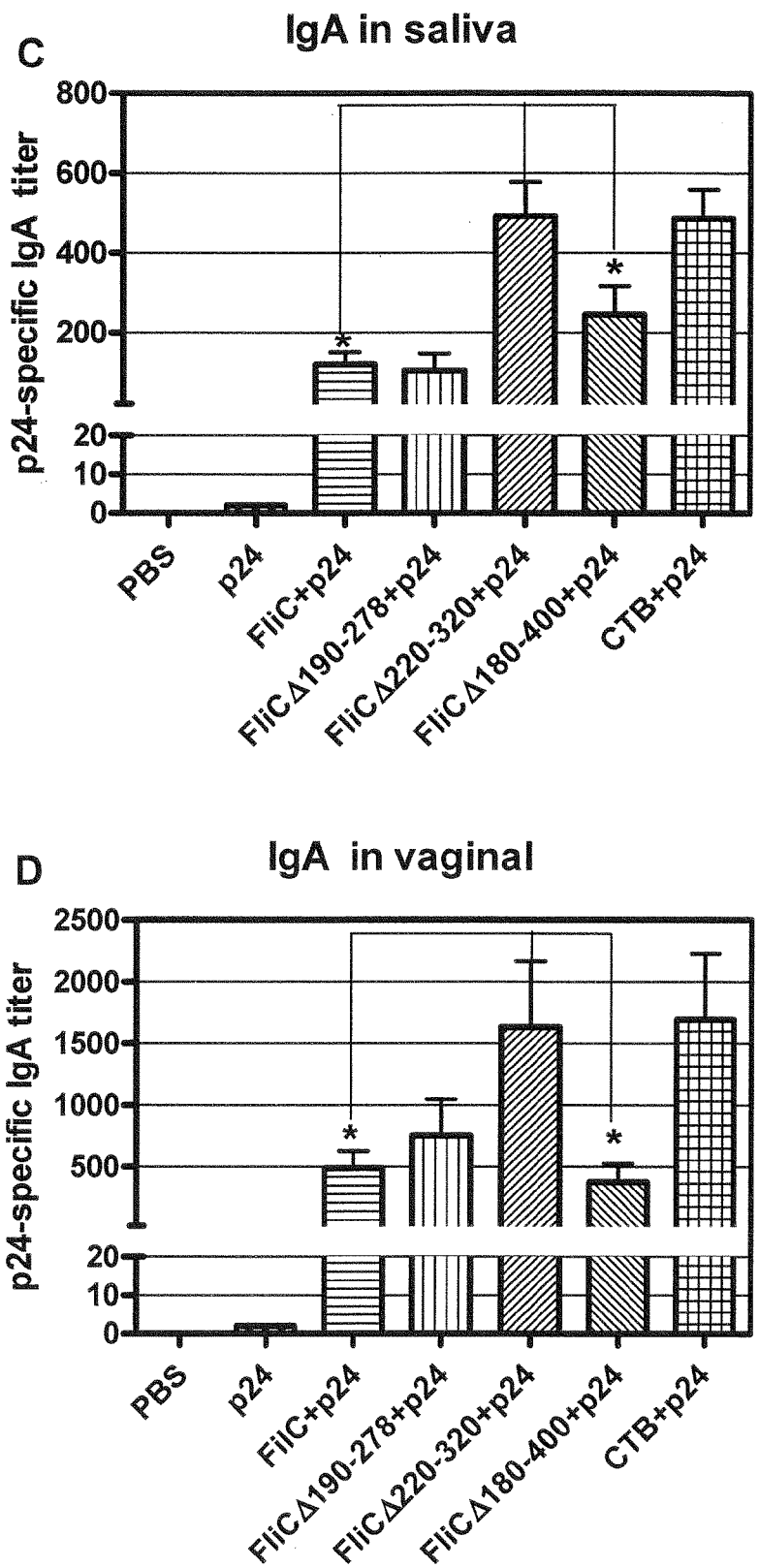

To further analyze the mucosal adjuvant activity of recombinant clones, p24 was used as antigen (10 μg/mouse) and mixed with FliC, FliCΔ190-278, FliCΔ220-320 or FliCΔ180-400 (2.5 μg/mouse) respectively, and then used to immunize the BALB/c mice. CTB adjuvant (2 μg/mouse) was positive control, and PBS or p24 was negative control. The BALB/c mice were booster immunized one time after 4 weeks, killed 2 weeks after the last immunization. The sera, saliva, vaginal samples were obtained to detect titer of p24-specific and adjuvant-specific antibody by ELISA. The result is shown in FIG. 7, FIG. 7 shows the result of titer detection of p24-specific and adjuvant-specific antibody in serum, saliva, vaginal samples by ELISA, with the p24 was used as antigen (10 μg/mouse) and mixed with FliC, FliCΔ190-278, FliCΔ220-320 and FliCΔ180-400 (2.5 μg/mouse) respectively, and then used to immune the BALB/c mice, wherein (A) shows the result of titer detection of p24-specific and adjuvant-specific IgG antibody in serum by ELISA, (B) shows the result of titer detection of p24-specific and adjuvant-specific IgA antibody in serum by ELISA, (C) shows the result of titer detection of p24-specific and adjuvant-specific IgA antibody in saliva by ELISA, (D) shows the result of titer detection of p24-specific and adjuvant-specific IgA antibody in vaginal by ELISA. Compared with control, flagellin deletion clones all had good adjuvant activity, wherein, the p24-specific IgG and IgA in serum of cloning FliCΔ220-320 immunized group had equivalent titer with that of full length flagellin FliC and CTB immunized group, with no significant difference. While the titer of p24-specific IgA in mucosa was significantly higher than that of full length flagellin FliC immunized group (p<0.05), equivalent with that of CTB immunized group, indicated good mucosal adjuvant activity (FIG. 7). The p24-specific IgG in serum of FliCΔ190-278 and FliCΔ180-400 was significantly lower than that of full length flagellin FliC immunized group, the IgA titer in serum and mucosal was equivalent with or slightly higher than that of FliC immunized group, while significantly lower than that of CTB immunized group (FIG. 7). Considering the above, the cloning FliCΔ220-320 was the better mucosal adjuvant than full length flagellin protein FliC.

Embodiment 9

FliCΔ220-320 Showed Higher Safety

Flagellin was an application-oriented new adjuvant, its safety was our greatest concern, while, there were many mutual contradictory reports about safety question of flagellin. It was reported in literature that flagellin was related to Crohn disease, lung cysts etc.; it was reported that flagellin had anti-tumor, anti-bacterial, anti-virus function by the research group of Vijay-Kumar and Burdelya etc. In light of this situation, our group carried out a preliminary research on acute toxicity of the flagellin. Methods refer to "Guiding principles of chemical drugs' acute toxicity experiment".

(I) Flagellin Had Potential Liver Acute Toxicity

Figure 8:
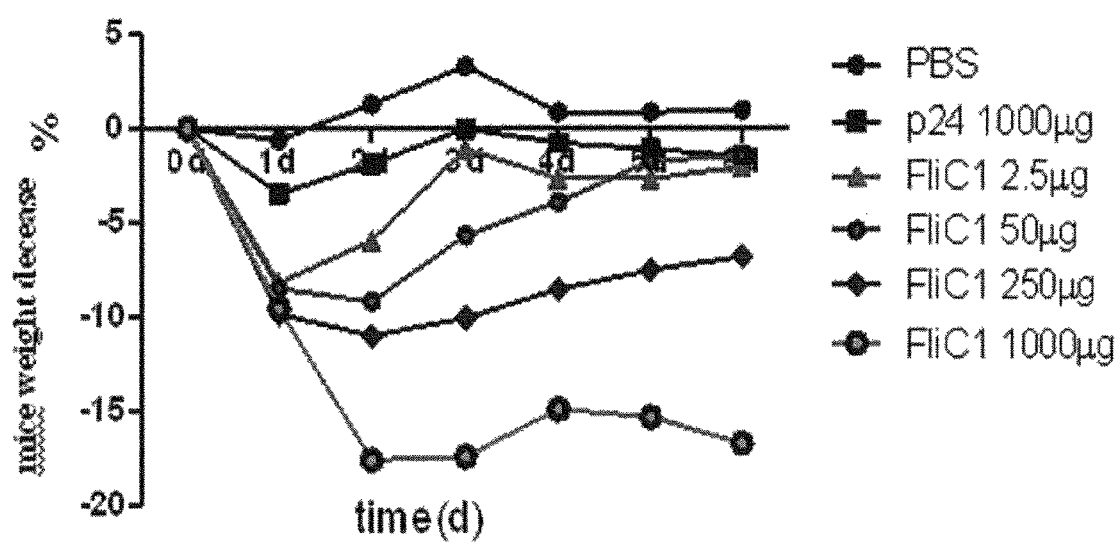
FIG. 8 shows the results of the weight changes after the mice were intranasally immunized, conventional fed after immunization, continuously observed for 7 days, and the weights of mice were daily recorded.

Preexamination: 6-8 weeks old BALB/c SFP female mice were selected for toxicity test, and were divided into 4 groups with different dose 2.5 μg, 50 μg, 250 μg and 1000 μg/mouse (conventional adjuvant dose of flagellin FliC1 was 2.5 μg, toxicity test dose was equivalent to 1 times, 20 times, 100 times and 400 times of the conventional adjuvant dose), 5 mice/group, and were intranasal immunized with the dose of 1000 μg/mouse. Negative control group were immunized with same volume of PBS, nonspecific protein control group were immunized with the HIV core antigen protein p24 which was purified in our laboratory. Conventional fed after immunization, continuous observed for 7 days, and the weight of mice and symptoms of animal toxicity reaction were daily recorded. Results: (1) observation of toxic symptoms: the FliC1 high dose group (that is 1000 μg/mouse) performed less spontaneous activity after the immunization for 48 h, fixed reposed with hair rough, reactivated at $48^{th}$ hour-72th hour, the spirit and foraging situation returned to normal after 72 h; the FliC1 low dose group of 2.5 μg/mouse and 50 μg/mouse showed normal activity as control group of p24 and PBS, had no significantly abnormal reaction. (2) changes of mice weight: the weight of FliC1 1000 μg group was severely lost, kept losing within 2 days after the immunization, and became lightest at the $2^{nd}$ day and the $3^{rd}$ day, the weight lost 20% compared with that before immunization, and became restored to some extent subsequently, while average lost 15% compared with that before immunization, and still not restored at the $6^{th}$ day; the weight of FliC1 250 μg group showed the same decrease trend as the 1000 μg group, but lost less with about 11% of weight, while became restored to some extent after the $3^{rd}$ day, average lost 6% compared with that before immunization; the weights of FliC1 2.5 μg group and 50 μg group were decreased for one day after immunization, average lost 20% compared with that before immunization, and became restored to some extent subsequently, restored to 98% of that before immunization; the weight of p24 group was decreased slightly compared to that before immunization, lost about 1%. The weight of PBS control group had not decreased during the immunization process. The result is shown in FIG. 8, FIG. 8 shows result figures of toxicity test preexamination, the mice were intranasal immunized, conventional fed after immunization, continuous observed for 7 days, and the weights of mice were daily recorded. Comprehensive considered the above two points: flagellin had dose-effect, barely effected at 2.5 μg/mouse, slightly effected at 50 μg/mouse within 24 h, the mice began to recover fastly after 24 h, and the dose of 250 μg and 1000 μg had severely toxicity to the mice, the toxicity of 250 μg was milder than that of 1000 μg. C57BL/6 mice showed the same reaction as that of BALB/c mice, and the data is not shown.

Formal tests: based on the above preexamination, for further analysis of the flagellin effect on every organs, the C57BL/6 mice were intranasal immunized with FliC1 250 μg, 5 mice/group, and the negative control were the mice without any treatment and the mice only immunized with PBS. They were killed respectively at $6^{th}$ hour, $12^{th}$ hour, $24^{th}$ hour, $36^{th}$ hour, $48^{th}$ hour, and a week after immunization. (1) Biochemical analyzed the biochemical indexes ALT and AST in serum reflecting liver injury, the biochemical indexes TP and ALB reflecting liver synthesis and reserve function, the TBiL and DBiL reflecting liver secretion and excretion function, and the BUN and CREA reflecting renal function lesions; (2) visual inspected possible pathological changes of mice organs in anatomization, and fixed and embedded the heart, liver, spleen, lung, renal and small intestine tissue, observed histopathological features of every organs after HE staining.

Figure 9:
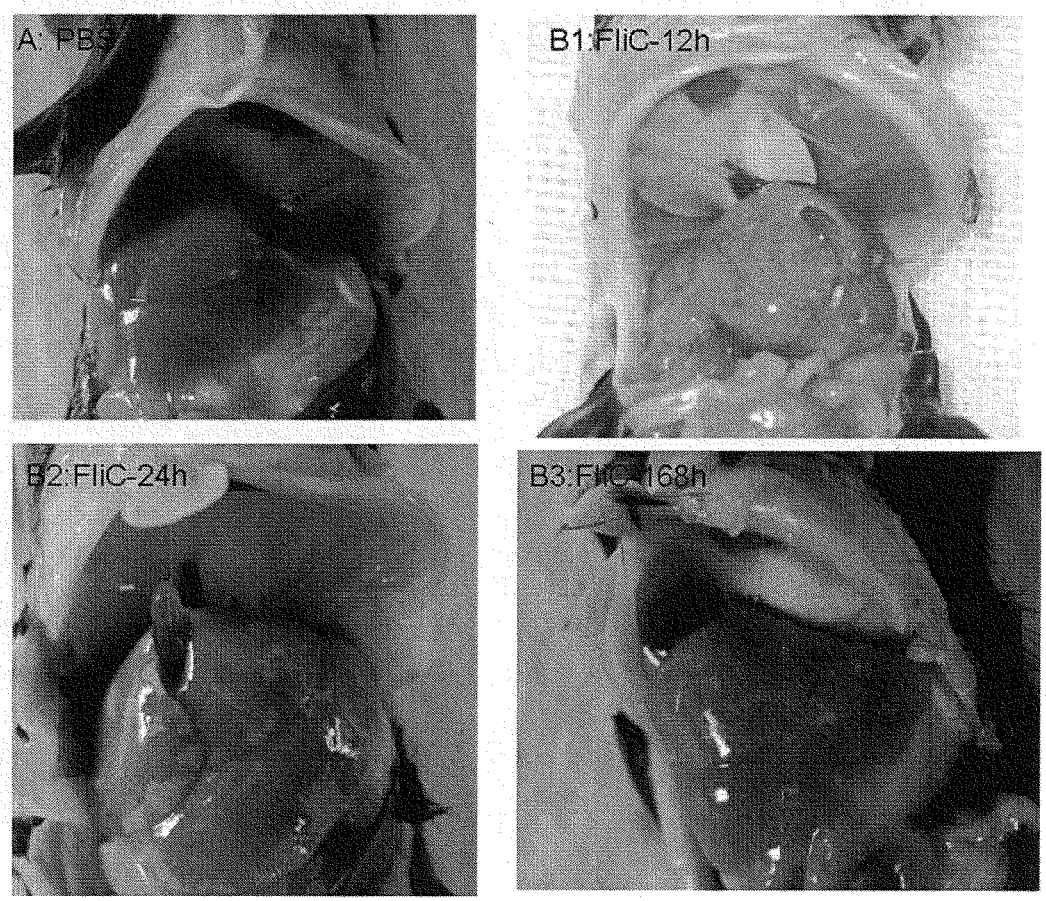
FIG. 9 shows the gross lesions of the livers from the C57BL/6 mice that were intranasally immunized with FliC1 and killed respectively at $12^{th}$ hour, $24^{th}$ hour, and a week after immunization, wherein (A) shows the gross appearance of the mouse liver of PBS group, (B1) the gross appearance of the mouse liver of treated group killed at 12th hour, (B2) the gross appearance of the mouse liver of treated group killed at 24th hour, and (B3) the gross appearance of the mouse liver of treated group killed at one week.

(1) system anatomical observation: related experiment result is shown in FIG. 9, FIG. 9 shows the liver lesions, the C57BL/6 mice were intranasal immunized with FliC1 and killed respectively at $6^{th}$ hour, $12^{th}$ hour, $24^{th}$ hour, $36^{th}$ hour, $48^{th}$ hour, and a week after immunization, wherein, figure A shows the result figure of anatomized mice liver surface of PBS group, figure B1 shows the result figure of liver surface of treated group killed at $12^{th}$ hour, figure B2 shows the result figure of liver surface of treated group killed at $24^{th}$ hour, figure B3 shows the result figure of liver surface of treated group killed at one week, figure C shows the comparison figure of observed histopathology of liver of FliC immunized group. When the mice were anatomized, the heart, liver, spleen, lung, renal and small intestine tissue had not been visual inspected lesion. The liver of FliC1 immunized group showed significant lesion, showed red spots on the surface of the liver at $12^{th}$ hour, the spots size were small, mainly focused on liver edge (FIG. 9, B1), the spots turned red to white and became bigger, extended from the edge toward the center, at $24^{th}$ hour the white spots were visible everywhere in the whole surface of the liver (FIG. 9, B2), and this phenomenon was kept until $48^{th}$ hour with the size and the number of the spots were reduce, the surface of the liver had not present significant white spots at one week (FIG. 9, B3). The surface of the mice liver of PBS group which were anatomized at the same time in process had not present any spot (FIG. 9, A).

Figure 10:
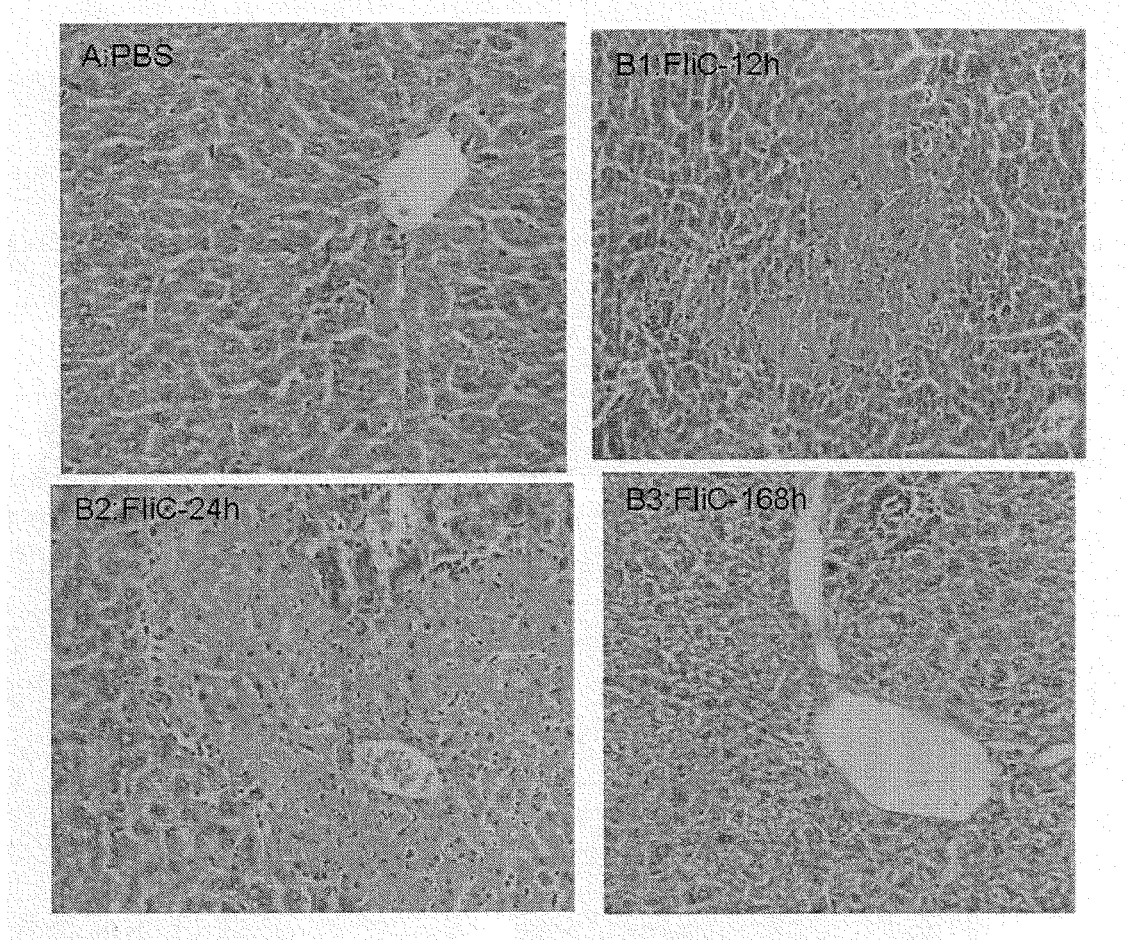
FIG. 10 shows the micro-lesions of mouse livers corresponding to the one shown in FIG. 9, wherein (A) shows the HE staining results of liver tissue of PBS group, (B1) the HE staining results of liver tissue of treated group killed at 12th hour, (B2) the HE staining results of liver tissue of treated group killed at 24th hour, and (B3) the HE staining results of liver tissue of treated group killed at one week.

(2) histopathological observation: after the above tissues were fixed with formalin, embedded in paraffin, and HE stained, the pathological changes of the tissues were observed. It is shown that: in the FliC1 immunized group, the heart, spleen, renal and small intestine tissues had not been pathological changed, the liver had severe lesion. The result is shown in FIG. 10, FIG. 10 shows liver lesion observed at different times of FliC1 immunized group, wherein, figure A shows the HE staining result figure of liver tissue of PBS group, figure B1 shows the HE staining result figure of liver tissue of treated group killed at $12^{th}$ hour, figure B2 shows the HE staining result figure of liver tissue of treated group killed at $24^{th}$ hour, figure B3 shows the HE staining result figure of anatomized mice liver tissue of treated group killed at one week. Specifically, the liver at $6^{th}$ hour had not present abnormality compared with the blank control group and the PBS control group, the livers at $12^{th}$ hour-$48^{th}$ hour had clear structures but turned out liver necrosis, and the liver necrosis accompanied with hemorrhage at $12^{th}$ (FIG. 10, B1), the liver at $24^{th}$ got worst, massive liver necrosed, and necrotic spot was large (FIG. 10, B2), and the livers at $36^{th}$ and $48^{th}$ had the same symptoms as that at $24^{th}$, while the symptoms at $24^{th}$ was mild, the liver of the mice anatomized at one week had not present necrotic spot, while the structure of liver cord and liver sinusoidal was not clear, the liver swelled and occurred vacuolar degeneration (FIG. 10, B3).

Figure 11:
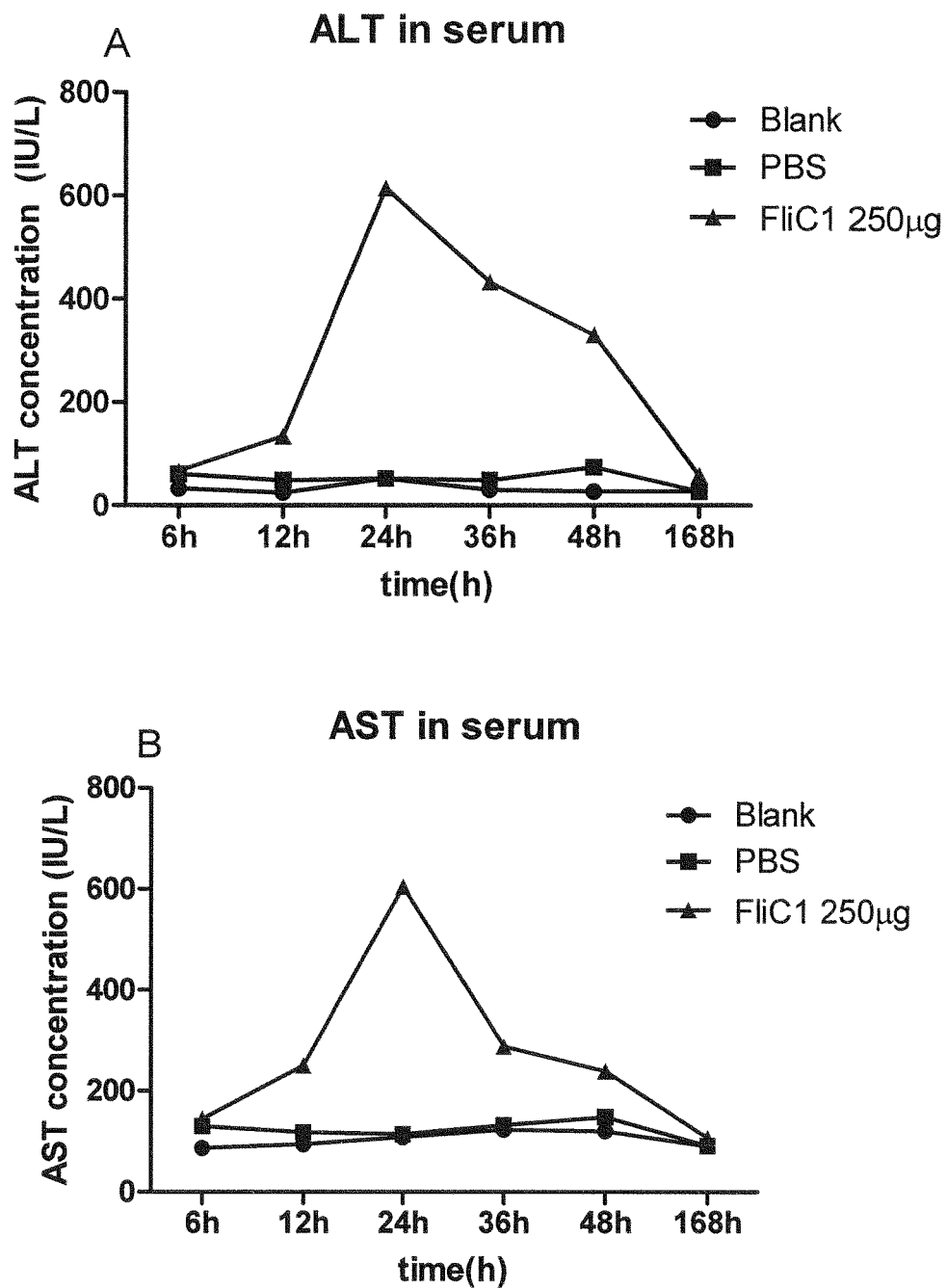
FIG. 11 shows the biochemical analysis results of biochemical indexes reflecting liver injury, using the sera of the FliC immunized group, wherein (A), (B), (C), (D), (E), (F), (G) and (H) were the biochemical analysis results of ALT, AST, TP, ALB, TBiL, DBiL, BUN and CREA, respectively.
Figure 11:
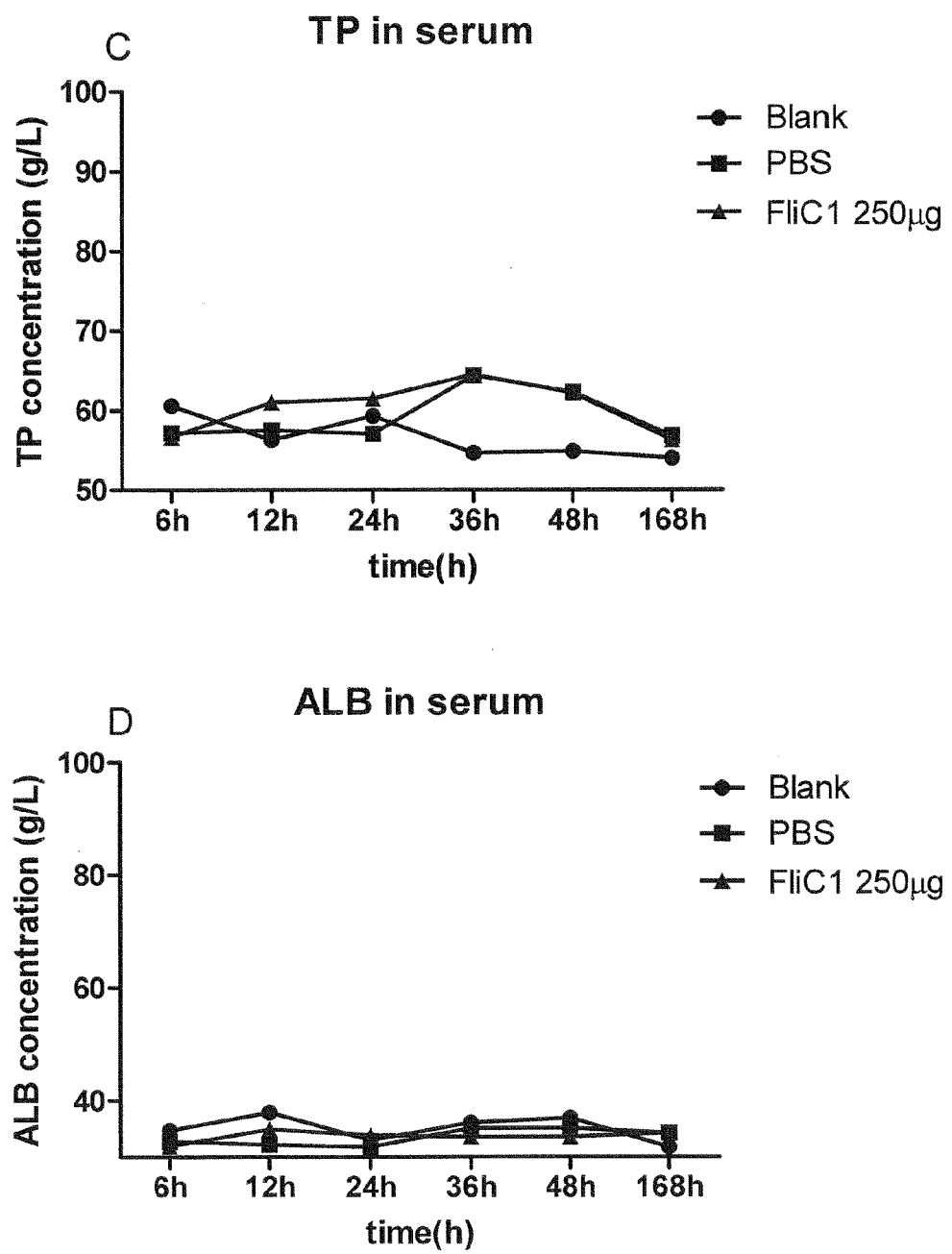
Figure 11:
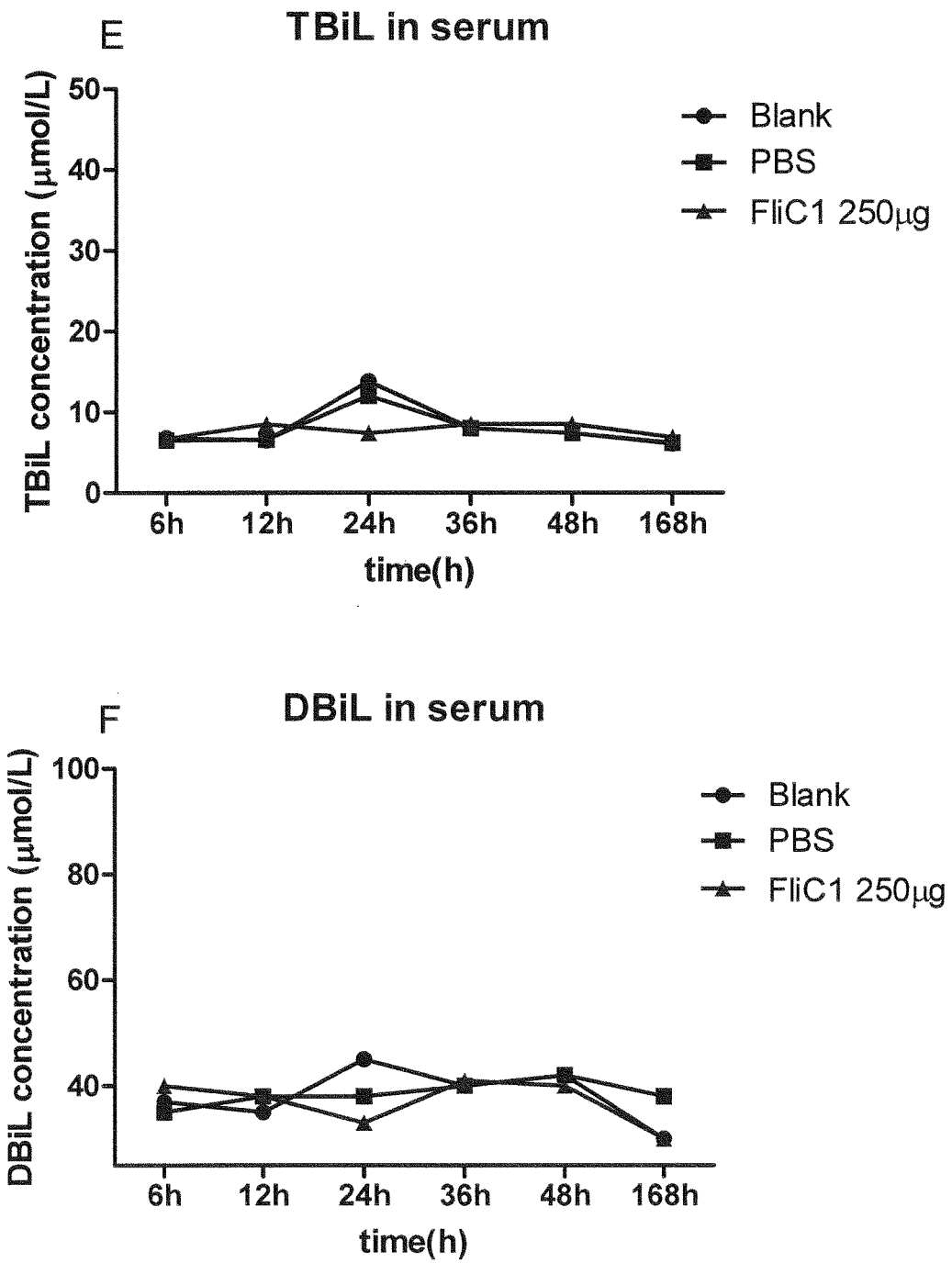
Figure 11:
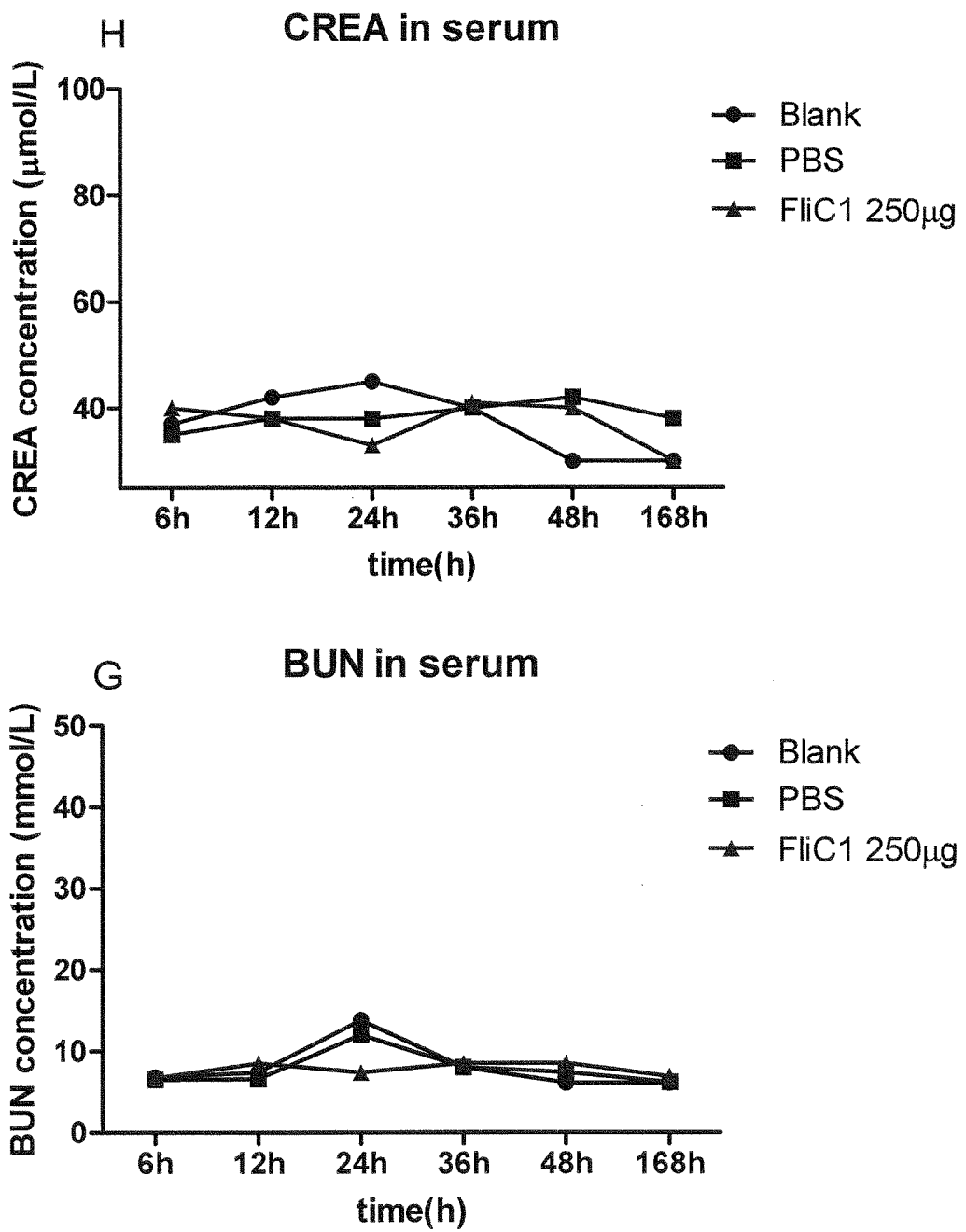

(3) Serum biochemical indexes analysis: according to the results of morphological and histopathological observation, the mice serum was biochemical analyzed (by biochemical analyzer), the result is shown in FIG. 11, FIG. 11 shows the biochemical analysis result figures of biochemical indexes reflecting liver injury, using the serum of the FliC1 immunized group, wherein, figure A, B, C, D, E, F, G and H were the biochemical analysis result figures of ALT, AST, TP, ALB, TBiL, DBiL, BUN and CREA, respectively. The figure shows that: in the serum of the FliC1 immunized group, the TP and ALB (FIG. 11, C and D), TBiL, DBiL (FIG. 11, E and F), and BUN, CREA (FIG. 11, G and H) were not differ from that of the blank control group and the PBS group. The ALT and AST values increased at the $12^{th}$ hour after the immunization, and reached the peak 600 IU/L at $24^{th}$ hour. The ALT and AST values increased significantly compared with that of the PBS group, 10 times and 4 times of that of PBS group, suggesting that massive liver cells were injured. The ALT and AST values decreased after $24^{th}$ hour, and reached the background level in one week after the immunization.

Comprehensively considered the above three points, the intranasal immunization with flagellin had severe liver toxicity.

Figure 12:
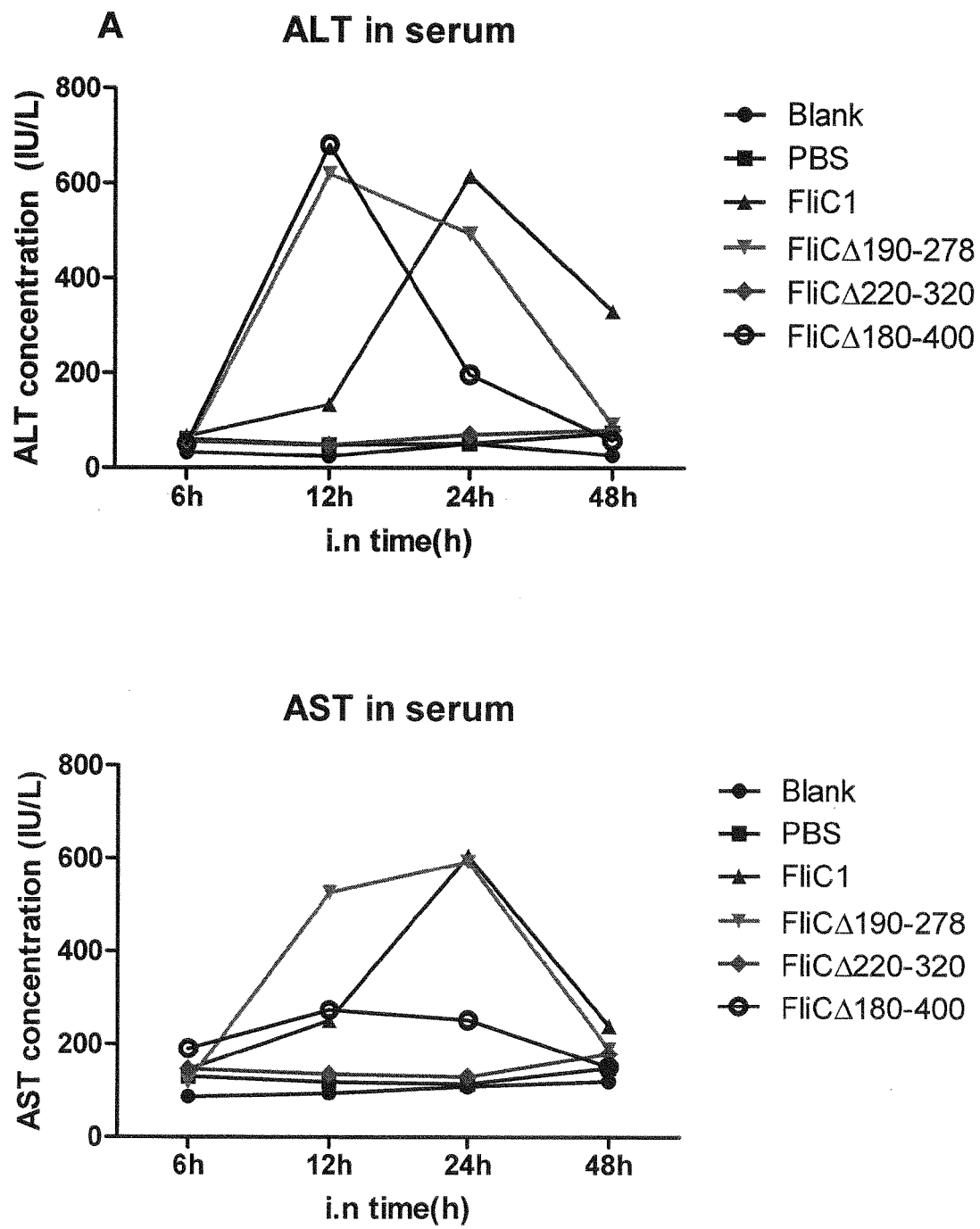
FIG. 12 shows related experiment results of FliCΔ220-320 safety, wherein (A) shows the comparison results of ALT and AST concentrations in the immunized sera of the FliC or different recombinant protein groups, (B) the gross appearance of the livers from the mice immunized with FliC or different recombinant proteins and killed at 24 hours post-immunization, and (C) the microscopic observations of liver lesions from the corresponding groups of (B).
Figure 12:
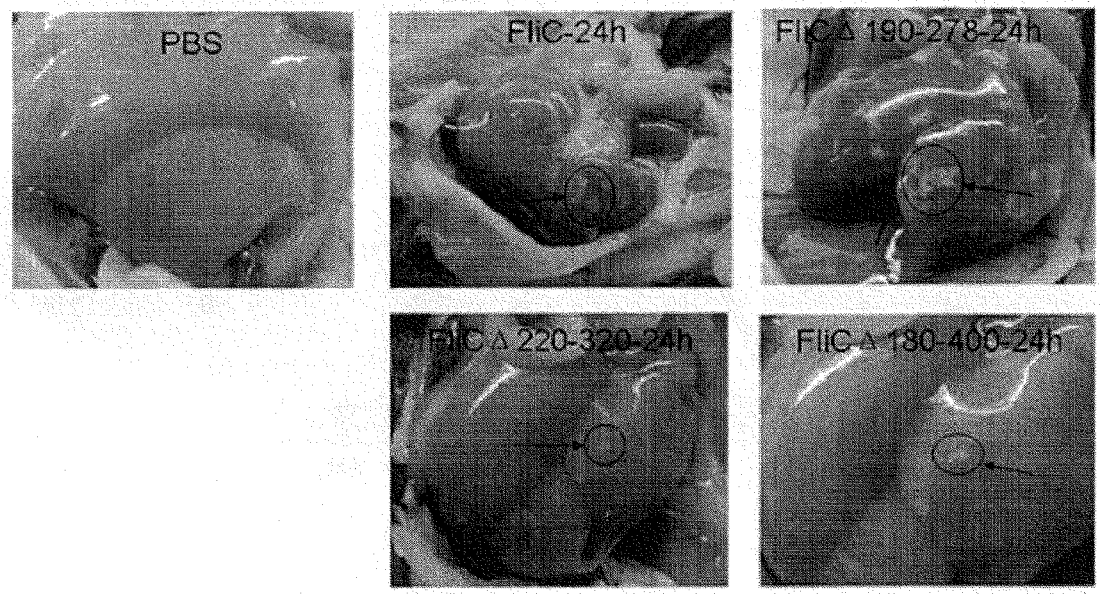
Figure 12:
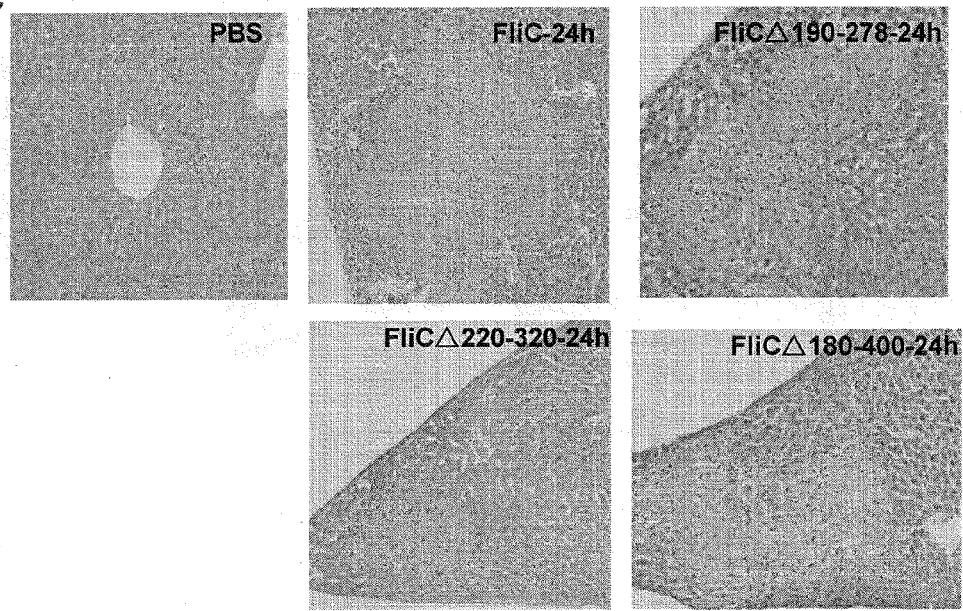

(II) FliCΔ220-320 significantly decreased liver toxicity compared with the full length flagellin To analyze the liver toxicity of deletion recombinant cloning and the full length flagellin, the C57BL/6 mice 6-8 weeks old were divided into 5 groups of blank control group, vehicle group (the PBS group), FliC, FliCΔ220-320 and FliCΔ180-400 group, and were intranasal immunized, 250 μg/mouse. The mice were kept fasting (not fasting in liquid) overnight before immunization, and were killed respectively at $6^{th}$ hour, $12^{th}$ hour, $24^{th}$ hour, $36^{th}$ hour, $48^{th}$ hour, and a week after immunization. The heart, liver, spleen, lung, renal and small intestine tissue were fixed and embedded, made into paraffin sections, observed histopathological changes of organs. The result is shown in FIG. 12, FIG. 12 shows related experiment results of FliCΔ220-320 safety, wherein, figure A shows the comparison figure of ALT and AST concentration in serum of the FliC immunized group, figure B shows the comparison figure of liver anatomical observation of the FliC immunized group, figure C shows the comparison figure of liver histopathological observation of the FliC immunized group. Specifically, the result is shown in FIG. 12: the ALT and AST values of the FliC immunized group increased 5-10 times of that of the blank control group and the PBS group, reached peak at $24^{th}$ hour, and decreased subsequently, and reached the background level in one week after the immunization; the ALT and AST values were equivalent in the FliCΔ190-278 immunized group and the FliC immunized group; the ALT value of the FliCΔ180-400 immunized group increased significantly, equivalent with the peak of the FliC immunized group, reached peak at $24^{th}$ hour, rapid decreased subsequently, and reached the background level at $48^{th}$ hour, while the AST value increased slightly from the $24^{th}$ hour to $36^{th}$ hour, and its peak value was 2-3 times of the blank control group and PBS group, and then decreased subsequently, and reached the background level at $48^{th}$ hour; the ALT and AST values of the FliCΔ220-320 immunized group had not rose during the process, were equivalent with the blank control group and the PBS group (FIG. 12, A); other biochemical indexes of flagellin FliC, FliCΔ220-320 and FliCΔ180-400 immunized group were not differ from the control group. (2) anatomical observation: the liver of FliC1 immunized group showed red spots on the surface of the liver at $12^{th}$ hour, the spots size were small, mainly focused on liver edge, and at $24^{th}$ hour the spots turned red to white and became bigger, extended from the edge toward the center, the white spots were visible everywhere in the whole surface of the liver, this phenomenon existed at $48^{th}$ hour, but the size and the number of the spots were reduce, the surface of the liver in the group killed at one week had not present significant white spots (FIG. 12, B). The symptoms of the FliCΔ190-278 immunized group were as the same as that of the FliC immunized group, with massive white necrotic spot presented on the surface of the liver. The surface of the mice liver of FliCΔ220-320 and FliCΔ180-400 immunized group which were anatomized at 24th hour-48th hour showed a few white spots, and the spots were small, at one week there was no white spot. (3) histopathological observation: liver: the FliC immunized group showed massive liver cell necrosis, accompanied with massive inflammatory cells infiltration, the symptoms were severely, especially in the phase of 24th hour-48th hour. It was almost anastomosed to the observation of anatomy (FIG. 12, C). The FliCΔ220-320 and FliCΔ180-400 immunized groups also showed liver cell necrosis in the phase of 24th hour-48th hour, but the necrotic foci appeared were only a few, the symptoms were mild. The other organs of flagellin immunized group showed no significant toxicity both in anatomical observation and histological observation. Comprehensive considered the biochemical indexes, the Flic anatomical observation and the histological observation, FliC showed potential acute toxicity of liver cells. Full deletion of hypervariable region, or deletion of hypervariable region in 220-320 amino acid sequences, significantly decreased the toxicity of flagellin. Comprehensive considered the biochemical indexes in serum, FliCΔ220-320 showed higher safety than FliC, FliCΔ190-278 and FliCΔ180-400.

In the above experiments, the operation of antibody titer detection in serum and mucosal by ELISA, were as follows:

the antigen was diluted to 3 μg/ml with coating buffer, 4° C. overnight; washed by 270/well, three times, 5 min each; blocked with blocking solution (PBS+0.05% Twee-20) 250 μg/well, incubated 1~2 h at 37° C.; the samples were gradient diluted by 4 times, and loaded into well, incubated 1~2 h at 37° C.; washed and added AP-conjugated secondary antibody (1:2000); incubated 1~2 h at 37° C.; washed and added AP chromogenic substrate; colored 30 min at 37° C., and OD405 absorption value was read. The antibody titer was defined as the maximum dilution multiple of serum when the optical absorption ratio >2.0 between the experimental group and the negative control group.

It should be noted that the scope of the present invention is not limited by the embodiments, while the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A recombinant flagellin protein FliCΔ220-320 represented by SEQ ID NO. 20.

2. The recombinant flagellin protein FliCΔ220-320 of claim 1, wherein the recombinant flagellin protein FliCΔ220-320 can be used as an adjuvant.

\* \* \* \* \*

```
                           SEQUENCE LISTING

<160> NUMBER OF SEQ ID NOS: 21

<210> SEQ ID NO 1
<211> LENGTH: 31
<212> TYPE: DNA
<213> ORGANISM: Artificial
<220> FEATURE:
<223> OTHER INFORMATION: Artificial sequence primer1

<400> SEQUENCE: 1
cgcgccatgg cacaagtcat taatacaaac a                              31

<210> SEQ ID NO 2
<211> LENGTH: 34
<212> TYPE: DNA
<213> ORGANISM: Artificial
<220> FEATURE:
<223> OTHER INFORMATION: Artificial sequence primer2

<400> SEQUENCE: 2
cggtctcgag acgcagtaaa gagaggacgt tttg                           34

<210> SEQ ID NO 3
<211> LENGTH: 29
<212> TYPE: DNA
<213> ORGANISM: Artificial
<220> FEATURE:
<223> OTHER INFORMATION: Artificial sequence primer13

<400> SEQUENCE: 3
cctacgccat ggcacaagtc attaataca                                 29

<210> SEQ ID NO 4
<211> LENGTH: 33
<212> TYPE: DNA
<213> ORGANISM: Artificial
<220> FEATURE:
<223> OTHER INFORMATION: Artificial sequence primer14

<400> SEQUENCE: 4
ggcagtgaat tctttatcaa cggttacagc agt                            33
```

<210> SEQ ID NO 5
<211> LENGTH: 33
<212> TYPE: DNA
<213> ORGANISM: Artificial
<220> FEATURE:
<223> OTHER INFORMATION: Artificial sequence primer15

<400> SEQUENCE: 5
cgatgcgaat tcataaccca caccaaatt gct                              33

<210> SEQ ID NO 6
<211> LENGTH: 33
<212> TYPE: DNA
<213> ORGANISM: Artificial
<220> FEATURE:
<223> OTHER INFORMATION: Artificial sequence primer16

<400> SEQUENCE: 6
gatccgctcg agacgcagta aagagaggac gtt                              33

<210> SEQ ID NO 7
<211> LENGTH: 29
<212> TYPE: DNA
<213> ORGANISM: Artificial
<220> FEATURE:
<223> OTHER INFORMATION: Artificial sequence primer17

<400> SEQUENCE: 7
cgcgttccat ggcacaagtc attaataca                                   29

<210> SEQ ID NO 8
<211> LENGTH: 33
<212> TYPE: DNA
<213> ORGANISM: Artificial
<220> FEATURE:
<223> OTHER INFORMATION: Artificial sequence primer18

<400> SEQUENCE: 8
ccagtagaat tcagtaaccc ccgttgcacc acc                              33

<210> SEQ ID NO 9
<211> LENGTH: 33
<212> TYPE: DNA
<213> ORGANISM: Artificial
<220> FEATURE:
<223> OTHER INFORMATION: Artificial sequence primer19

<400> SEQUENCE: 9
ccagtggaat tctttgagga taaaaacggt aag                              33

<210> SEQ ID NO 10
<211> LENGTH: 36
<212> TYPE: DNA
<213> ORGANISM: Artificial
<220> FEATURE:
<223> OTHER INFORMATION: Artificial sequence primer20

<400> SEQUENCE: 10
gccgatctcg agacgcagta aagagaggac gttttg                           36

<210> SEQ ID NO 11
<211> LENGTH: 29
<212> TYPE: DNA
<213> ORGANISM: Artificial
<220> FEATURE:
<223> OTHER INFORMATION: Artificial sequence primer21

-continued

<400> SEQUENCE: 11
cgcgttccat ggcacaagtc attaataca                                  29

<210> SEQ ID NO 12
<211> LENGTH: 33
<212> TYPE: DNA
<213> ORGANISM: Artificial
<220> FEATURE:
<223> OTHER INFORMATION: Artificial sequence primer22

<400> SEQUENCE: 12
ggcttggaat tcggtgtagg catcttggac att                             33

<210> SEQ ID NO 13
<211> LENGTH: 33
<212> TYPE: DNA
<213> ORGANISM: Artificial
<220> FEATURE:
<223> OTHER INFORMATION: Artificial sequence primer23

<400> SEQUENCE: 13
ggcacggaat tcaacttcag aacaggcggt gag                             33

<210> SEQ ID NO 14
<211> LENGTH: 36
<212> TYPE: DNA
<213> ORGANISM: Artificial
<220> FEATURE:
<223> OTHER INFORMATION: Artificial sequence primer24

<400> SEQUENCE: 14
gccgatctcg agacgcagta aagagaggac gttttg                          36

<210> SEQ ID NO 15
<211> LENGTH: 32
<212> TYPE: DNA
<213> ORGANISM: Artificial
<220> FEATURE:
<223> OTHER INFORMATION: Artificial sequence primer31

<400> SEQUENCE: 15
ctcgatccat ggttgcggct caacttgctg ca                              32

<210> SEQ ID NO 16
<211> LENGTH: 33
<212> TYPE: DNA
<213> ORGANISM: Artificial
<220> FEATURE:
<223> OTHER INFORMATION: Artificial sequence primer32

<400> SEQUENCE: 16
ggctgactcg agtgcgtagt cggaatcttc gat                             33

<210> SEQ ID NO 17
<211> LENGTH: 506
<212> TYPE: PRT
<213> ORGANISM: Salmonella enterica

<400> SEQUENCE: 17

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

```
Ala Ile Ala Asn Arg Phe Thr Ala Asn Ile Lys Gly Leu Thr Gln Ala
     50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Asn Leu Gln Arg Val Arg Glu Leu Ala
                 85                  90                  95

Val Gln Ser Ala Asn Gly Thr Asn Ser Gln Ser Asp Leu Asp Ser Ile
                100                 105                 110

Gln Ala Glu Ile Thr Gln Arg Leu Asn Glu Ile Asp Arg Val Ser Gly
            115                 120                 125

Gln Thr Gln Phe Asn Gly Val Lys Val Leu Ala Gln Asp Asn Thr Leu
        130                 135                 140

Thr Ile Gln Val Gly Ala Asn Asp Gly Glu Thr Ile Asp Ile Asp Leu
145                 150                 155                 160

Lys Glu Ile Ser Ser Lys Thr Leu Gly Leu Asp Lys Leu Asn Val Gln
                165                 170                 175

Asp Ala Tyr Thr Pro Lys Glu Thr Ala Val Thr Val Asp Lys Thr Thr
            180                 185                 190

Tyr Lys Asn Gly Thr Asp Pro Ile Thr Ala Gln Ser Asn Thr Asp Ile
        195                 200                 205

Gln Thr Ala Ile Gly Gly Gly Ala Thr Gly Val Thr Gly Ala Asp Ile
    210                 215                 220

Lys Phe Lys Asp Gly Gln Tyr Tyr Leu Asp Val Lys Gly Gly Ala Ser
225                 230                 235                 240

Ala Gly Val Tyr Lys Ala Thr Tyr Asp Glu Thr Thr Lys Lys Val Asn
                245                 250                 255

Ile Asp Thr Thr Asp Lys Thr Pro Leu Ala Thr Ala Glu Ala Thr Ala
            260                 265                 270

Ile Arg Gly Thr Ala Thr Ile Thr His Asn Gln Ile Ala Glu Val Thr
        275                 280                 285

Lys Glu Gly Val Asp Thr Thr Val Ala Ala Gln Leu Ala Ala Ala Ala
    290                 295                 300

Gly Val Thr Gly Ala Asp Lys Asp Asn Thr Ser Leu Val Lys Leu Ser
305                 310                 315                 320

Phe Glu Asp Lys Asn Gly Lys Val Ile Asp Gly Gly Tyr Ala Val Lys
                325                 330                 335

Met Gly Asp Asp Phe Tyr Ala Ala Thr Tyr Asp Glu Lys Thr Gly Ala
            340                 345                 350

Ile Thr Ala Lys Thr Thr Thr Tyr Thr Asp Gly Thr Gly Val Ala Gln
        355                 360                 365

Thr Gly Ala Val Lys Phe Gly Gly Ala Asn Gly Lys Ser Glu Val Val
    370                 375                 380

Thr Ala Thr Asp Gly Lys Thr Tyr Leu Ala Ser Asp Leu Asp Lys His
385                 390                 395                 400

Asn Phe Arg Thr Gly Gly Glu Leu Lys Glu Val Asn Thr Asp Lys Thr
                405                 410                 415

Glu Asn Pro Leu Gln Lys Ile Asp Ala Ala Leu Ala Gln Val Asp Thr
            420                 425                 430

Leu Arg Ser Asp Leu Gly Ala Val Gln Asn Arg Phe Asn Ser Ala Ile
        435                 440                 445

Thr Asn Leu Gly Asn Thr Val Asn Asn Leu Ser Ser Ala Arg Ser Arg
    450                 455                 460

Ile Glu Asp Ser Asp Tyr Ala Thr Glu Val Ser Asn Met Ser Arg Ala
```

```
                465                 470                 475                 480
        Gln Ile Leu Gln Gln Ala Gly Thr Ser Val Leu Ala Gln Ala Asn Gln
                            485                 490                 495

Val Pro Gln Asn Val Leu Ser Leu Leu Arg
                    500                 505

<210> SEQ ID NO 18
<211> LENGTH: 288
<212> TYPE: PRT
<213> ORGANISM: Salmonella enterica

<400> SEQUENCE: 18

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Gly Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Glu Ile Ser Ser Lys Thr Leu Gly Leu Asp Lys Leu Asn Val Gln
                165                 170                 175

Asp Ala Tyr Thr Glu Phe Asn Phe Arg Thr Gly Gly Glu Leu Lys Glu
            180                 185                 190

Val Asn Thr Asp Lys Thr Glu Asn Pro Leu Gln Lys Ile Asp Ala Ala
        195                 200                 205

Leu Ala Gln Val Asp Thr Leu Arg Ser Asp Leu Gly Ala Val Gln Asn
    210                 215                 220

Arg Phe Asn Ser Ala Ile Thr Asn Leu Gly Asn Thr Val Asn Asn Leu
225                 230                 235                 240

Ser Ser Ala Arg Ser Arg Ile Glu Asp Ser Asp Tyr Ala Thr Glu Val
                245                 250                 255

Ser Asn Met Ser Arg Ala Gln Ile Leu Gln Gln Ala Gly Thr Ser Val
            260                 265                 270

Leu Ala Gln Ala Asn Gln Val Pro Gln Asn Val Leu Ser Leu Leu Arg
        275                 280                 285

<210> SEQ ID NO 19
<211> LENGTH: 420
<212> TYPE: PRT
<213> ORGANISM: Salmonella enterica

<400> SEQUENCE: 19

Met Ala Gln Val Ile Asn Thr Asn Ser Leu Ser Leu Leu Thr Gln Asn
1               5                   10                  15
```

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ala
                85                  90                  95

Val Gln Ser Ala Asn Gly Thr Asn Ser Gln Ser Asp Leu Asp Ser Ile
            100                 105                 110

Gln Ala Glu Ile Thr Gln Arg Leu Asn Glu Ile Asp Arg Val Ser Gly
            115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Glu Ile Ser Ser Lys Thr Leu Gly Leu Asp Lys Leu Asn Val Gln
                165                 170                 175

Asp Ala Tyr Thr Pro Lys Glu Thr Ala Val Thr Val Ser Lys Glu Phe
            180                 185                 190

Ile Thr His Asn Gln Ile Ala Glu Val Thr Lys Glu Gly Val Asp Thr
        195                 200                 205

Thr Thr Val Ala Ala Gln Leu Ala Ala Gly Val Thr Gly Ala Asp
210                 215                 220

Lys Asp Asn Thr Ser Leu Val Lys Leu Ser Phe Glu Asp Lys Asn Gly
225                 230                 235                 240

Lys Val Ile Asp Gly Gly Tyr Ala Val Lys Met Gly Asp Asp Phe Tyr
            245                 250                 255

Ala Ala Thr Tyr Asp Glu Lys Thr Gly Ala Ile Thr Ala Lys Thr Thr
        260                 265                 270

Thr Tyr Thr Asp Gly Thr Gly Val Ala Gln Thr Gly Ala Val Lys Phe
    275                 280                 285

Gly Gly Ala Asn Gly Lys Ser Glu Val Val Thr Ala Thr Asp Gly Lys
290                 295                 300

Thr Tyr Leu Ala Ser Asp Leu Asp Lys His Asn Phe Arg Thr Gly Gly
305                 310                 315                 320

Glu Leu Lys Glu Val Asn Thr Asp Lys Thr Glu Asn Pro Leu Gln Lys
            325                 330                 335

Ile Asp Ala Ala Leu Ala Gln Val Asp Thr Leu Arg Ser Asp Leu Gly
        340                 345                 350

Ala Val Gln Asn Arg Phe Asn Ser Ala Ile Thr Asn Leu Gly Asn Thr
    355                 360                 365

Val Asn Asn Leu Ser Ser Ala Arg Ser Arg Ile Glu Asp Ser Asp Tyr
370                 375                 380

Ala Thr Glu Val Ser Asn Met Ser Arg Ala Gln Ile Leu Gln Gln Ala
385                 390                 395                 400

Gly Thr Ser Val Leu Ala Gln Ala Asn Gln Val Pro Gln Asn Val Leu
            405                 410                 415

Ser Leu Leu Arg
            420

<210> SEQ ID NO 20
<211> LENGTH: 408
<212> TYPE: PRT
<213> ORGANISM: Salmonella enterica

<400> SEQUENCE: 20

```
Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ala
                85                  90                  95

Val Gln Ser Ala Asn Gly Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Glu Ile Ser Ser Lys Thr Leu Gly Leu Asp Lys Leu Asn Val Gln
                165                 170                 175

Asp Ala Tyr Thr Pro Lys Glu Thr Ala Val Thr Val Asp Lys Thr Thr
            180                 185                 190

Tyr Lys Asn Gly Thr Asp Pro Ile Thr Ala Gln Ser Asn Thr Asp Ile
        195                 200                 205

Gln Thr Ala Ile Gly Gly Gly Ala Thr Gly Val Thr Glu Phe Phe Glu
    210                 215                 220

Asp Lys Asn Gly Lys Val Ile Asp Gly Gly Tyr Ala Val Lys Met Gly
225                 230                 235                 240

Asp Asp Phe Tyr Ala Ala Thr Tyr Asp Glu Lys Thr Gly Ala Ile Thr
                245                 250                 255

Ala Lys Thr Thr Thr Tyr Thr Asp Gly Thr Gly Val Ala Gln Thr Gly
            260                 265                 270

Ala Val Lys Phe Gly Gly Ala Asn Gly Lys Ser Glu Val Val Thr Ala
        275                 280                 285

Thr Asp Gly Lys Thr Tyr Leu Ala Ser Asp Leu Asp Lys His Asn Phe
    290                 295                 300

Arg Thr Gly Gly Glu Leu Lys Glu Val Asn Thr Asp Lys Thr Glu Asn
305                 310                 315                 320

Pro Leu Gln Lys Ile Asp Ala Ala Leu Ala Gln Val Asp Thr Leu Arg
                325                 330                 335

Ser Asp Leu Gly Ala Val Gln Asn Arg Phe Asn Ser Ala Ile Thr Asn
            340                 345                 350

Leu Gly Asn Thr Val Asn Asn Leu Ser Ser Ala Arg Ser Arg Ile Glu
        355                 360                 365

Asp Ser Asp Tyr Ala Thr Glu Val Ser Asn Met Ser Arg Ala Gln Ile
    370                 375                 380

Leu Gln Gln Ala Gly Thr Ser Val Leu Ala Gln Ala Asn Gln Val Pro
```

```
<210> SEQ ID NO 21
<211> LENGTH: 175
<212> TYPE: PRT
<213> ORGANISM: Salmonella enterica

<400> SEQUENCE: 21

Val Ala Ala Gln Leu Ala Ala Ala Gly Val Thr Gly Ala Asp Lys Asp
1               5                   10                  15

Asn Thr Ser Leu Val Lys Leu Ser Phe Glu Asp Lys Asn Gly Lys Val
            20                  25                  30

Ile Asp Gly Gly Tyr Ala Val Lys Met Gly Asp Asp Phe Tyr Ala Ala
        35                  40                  45

Thr Tyr Asp Glu Lys Thr Gly Ala Ile Thr Ala Lys Thr Thr Thr Tyr
    50                  55                  60

Thr Asp Gly Thr Gly Val Ala Gln Thr Gly Ala Val Lys Phe Gly Gly
65                  70                  75                  80

Ala Asn Gly Lys Ser Glu Val Val Thr Ala Thr Asp Gly Lys Thr Tyr
                85                  90                  95

Leu Ala Ser Asp Leu Asp Lys His Asn Phe Arg Thr Gly Gly Glu Leu
            100                 105                 110

Lys Glu Val Asn Thr Asp Lys Thr Glu Asn Pro Leu Gln Lys Ile Asp
        115                 120                 125

Ala Ala Leu Ala Gln Val Asp Thr Leu Arg Ser Asp Leu Gly Ala Val
    130                 135                 140

Gln Asn Arg Phe Asn Ser Ala Ile Thr Asn Leu Gly Asn Thr Val Asn
145                 150                 155                 160

Asn Leu Ser Ser Ala Arg Ser Arg Ile Glu Asp Ser Asp Tyr Ala
                165                 170                 175
```